US012778516B2

(12) United States Patent
Loddenkemper et al.

(10) Patent No.: US 12,778,516 B2
(45) Date of Patent: Nov. 3, 2026

(54) COMPUTER-BASED SYSTEMS AND DEVICES CONFIGURED FOR DEEP LEARNING FROM SENSOR DATA NON-INVASIVE SEIZURE FORECASTING AND METHODS THEREOF

(71) Applicant: The Children's Medical Center Corporation, Boston, MA (US)

(72) Inventors: Tobias Loddenkemper, Boston, MA (US); Christian Meisel, Boston, MA (US)

(73) Assignee: The Children's Medical Center Corporation, Boston, MA (US)

( * ) Notice: Subject to any disclaimer, the term of this patent is extended or adjusted under 35 U.S.C. 154(b) by 697 days.

(21) Appl. No.: 17/915,911

(22) PCT Filed: Mar. 31, 2021

(86) PCT No.: PCT/US2021/025084
§ 371 (c)(1),
(2) Date: Sep. 29, 2022

(87) PCT Pub. No.: WO2021/202661
PCT Pub. Date: Oct. 7, 2021

(65) Prior Publication Data

US 2023/0141496 A1 May 11, 2023

Related U.S. Application Data

(60) Provisional application No. 63/004,611, filed on Apr. 3, 2020.

(51) Int. Cl.
*A61B 5/00* (2006.01)
*G16H 40/67* (2018.01)
*G16H 50/30* (2018.01)

(52) U.S. Cl.
CPC .......... *A61B 5/7275* (2013.01); *A61B 5/4094* (2013.01); *A61B 5/681* (2013.01);
(Continued)

(58) Field of Classification Search
CPC ..... A61B 5/4094; A61B 5/369; A61B 5/7264; A61B 5/7275; A61B 5/7267;
(Continued)

(56) References Cited

U.S. PATENT DOCUMENTS 10,463,270 B2 * 11/2019 Leyde .................. A61B 5/0006
2007/0213786 A1 * 9/2007 Sackellares ............ A61B 5/369
607/45

(Continued)

OTHER PUBLICATIONS

Reilly, E. D., Ralston, A., & Hemmendinger, D. (Eds.). (2003). Machine learning. In Encyclopedia of Computer Science</i> (4th ed.). Wiley. https://search.credoreference.com/articles/Qm9va0FydGljbGU6MTY2NTU0Nw==?aid=279753 (Year: 2003).*

(Continued)

*Primary Examiner* — Deborah L Malamud
(74) *Attorney, Agent, or Firm* — Greenberg Traurig, LLP; Melissa Hunter-Ensor; Kristopher Reichlen

(57) ABSTRACT

To enable real-time seizure warnings, systems and methods of the present disclosure include a wearable sensor in communication with processors that are configured to receive from the wearable sensor data streams associated with a user that include biomarker data parameters.

18 Claims, 17 Drawing Sheets

(52) U.S. Cl.
CPC ............ *A61B 5/7267* (2013.01); *A61B 5/746* (2013.01); *G16H 40/67* (2018.01); *G16H 50/30* (2018.01)

(58) Field of Classification Search
CPC ..... A61B 5/0006; A61B 5/316; A61B 5/7282; A61B 5/486; A61B 5/7246; A61B 5/372; A61B 5/291; A61B 5/4064; A61B 5/37; A61B 5/31; A61B 5/24; A61N 1/36064; A61N 1/36135
See application file for complete search history.

(56) References Cited

U.S. PATENT DOCUMENTS

| | | | |
|---|---|---|---|
| 2014/0257128 | A1 | 9/2014 | Moxon et al. |
| 2016/0206236 | A1 | 7/2016 | DiLorenzo et al. |
| 2019/0150774 | A1 | 5/2019 | Brinkmann et al. |
| 2019/0246990 | A1 | 8/2019 | Karoly et al. |
| 2019/0298248 | A1 | 10/2019 | Loddenkemper et al. |

OTHER PUBLICATIONS

International Search Report and Written Opinion mailed Aug. 24, 2021 in corresponding International PCT Patent Application No. PCT/US2021/025084 (14 pages).

* cited by examiner

COMPUTER-BASED SYSTEMS AND DEVICES CONFIGURED FOR DEEP LEARNING FROM SENSOR DATA NON-INVASIVE SEIZURE FORECASTING AND METHODS THEREOF

CROSS-REFERENCE To RELATED APPLICATION

This application is the U.S. National Stage Application, pursuant to 35 U.S.C. § 371 of PCT International Application No. PCT/US2021/025084, filed Mar. 31, 2021, designating the United States and published in English, which claims priority to and the benefit of U.S. Provisional Patent Application No. 63/004,611, filed Apr. 3, 2020, the contents of all of which are hereby incorporated by reference in their entirety.

BACKGROUND OF TECHNOLOGY

Reliable methods to assess seizure risk could alleviate a major burden for epilepsy patients by providing timely warning or relief when seizure risk is high or low. From a clinician perspective, robust seizure risk assessments are desirable because of their ability to improve treatment by optimizing dosing and timing of antiseizure medication regimen utilizing objective, personalized standards, as well as by potentially enabling timely interventions to avert impending seizures. Following initial attempts, there has been a recent surge of studies demonstrating the possibility of accurate seizure forecasting. To this end, most studies have utilized either electrocorticography (ECoG) or scalp electroencephalography (EEG) as well as, to a lesser extent, electrocardiography (ECG), and have demonstrated that robust differentiation between preictal and interictal periods is possible with a performance better than chance. Furthermore, seizure forecasting has traditionally performed best when algorithms were trained or optimized at the individual patient level, which often required some sort of training or adjustment phase prior to deployment.

SUMMARY OF DESCRIBED USER MATTER

Seizure forecasting may provide patients with timely warnings to adapt their daily activities and help clinicians deliver more objective, personalized treatments. While recent work has convincingly demonstrated that seizure risk assessment is in principle possible, these early approaches relied largely on complex, often invasive setups including intracranial electrocorticography, implanted devices and multi-channel EEG, and required patient-specific adaptation or learning to perform optimally, all of which limit translation to broad clinical application. To facilitate broader adaptation of seizure forecasting in clinical practice, non-invasive, easily applicable techniques that reliably assess seizure risk without much prior tuning are crucial. Wearable sensors that continuously record physiological parameters, including electrodermal activity, body temperature, blood volume pulse and actigraphy, may afford monitoring of autonomous nervous system function and movement relevant for such a task, hence minimizing potential complications associated with invasive monitoring, and avoiding stigma associated with bulky external monitoring devices on the head. Here, we applied deep learning on multi-modal wearable sensor data from 69 patients with epilepsy (total duration >2311 hours, 452 seizures) to assess its capability to forecast seizures in a clinically meaningful way. Using a leave-one-out cross-validation approach we identified better-than-chance, clinically meaningful predictability in out-of-sample test data in about half of the patients. Prediction performance increased with the size of the training dataset indicating that our approach will improve further with larger datasets in the future. Collectively, these results show for the first time that clinically meaningful seizure risk assessments are feasible from easy-to-use, non-invasive wearable devices without the need of patient-specific training or parameter optimization.

In some embodiments, the present disclosure provides an exemplary technically improved computer-based method that includes at least the following steps of receiving, by at least one processor, at least one data stream including wearable sensor data associated with a user; where the at least one data stream includes biomarker data parameters; utilizing, by the at least one processor, seizure forecasting machine learning model to predict a pre-ictal period probability associated with a forecasted time segment based at least in part on values of the at least one data stream; determining, by the at least one processor, a segment for an integration window of a history pre-ictal period probabilities for the forecasted time segment and at least one previously forecasted time segment; determining, by the at least one processor, a pre-ictal period based at least in part on the segment exceeding a pre-ictal probability threshold; determining, by the at least one processor, a pre-ictal risk indication including a seizure treatment administration responsive to the pre-ictal risk indication; and causing to produce, by the at least one processor, the pre-ictal risk indication at a computing device associated with the user to alert the user of a predicted risk of a seizure.

In some embodiments, the present disclosure provides another exemplary technically improved computer-based system that includes at least the following components of at least one sensor, and at least one processor in communication with the at least one sensor. The at least one processor is configured to perform steps of instructions stored in a non-transitory memory, the steps including: receive from the at least one sensor at least one data stream associated with a user; where the at least one data stream includes biomarker data parameters; utilize seizure forecasting machine learning model to predict a pre-ictal period probability associated with a forecasted time segment based at least in part on values of the at least one data stream; determine a segment average for an integration window of a history pre-ictal period probabilities for the forecasted time segment and at least one previously forecasted time segment; determine a pre-ictal period based at least in part on the segment average exceeding a pre-ictal probability threshold; determine a pre-ictal risk indication including a seizure treatment administration responsive to the pre-ictal risk indication; and cause to produce the pre-ictal risk indication at a computing device associated with the user to indicate a predicted risk of a seizure.

In some embodiments, the present disclosure provides another exemplary technically improved computer-based method that includes at least the following steps of receiving, by at least one processor, a training dataset from a plurality of ground-truth time-series electrophysiological datasets; where each ground-truth time-series electrophysiological data of the plurality of ground-truth time-series electrophysiological datasets includes a series of labelled epochs; determining, by the at least one processor, an epoch average of electrophysiological data values in each labelled epoch of each series of labelled epochs of each ground-truth time-series electrophysiological data; training, by the at least one processor, a seizure forecasting machine learning model using leave-one-out cross validation with the training datasets based on labels associated with each labelled epoch and the epoch average associated with each labelled epoch; where the machine learning model is trained on data from single or multiple patients to predict a pre-ictal period probability associated with a forecasted time segment based at least in part on values of the at least one data stream; where optimal values for integration window, a time span of the forecasted time segment, a pre-ictal probability threshold, a seizure occurrence period, or combinations thereof are determined from the training set data or are set according to individual preference; storing, by the at least one processor, the regression machine learning model in a memory upon being trained to predict the pre-ictal period probability.

Embodiments of the present disclosure further include generating a pre-ictal risk alert to alert the user of the predicted seizure.

Embodiments of the present disclosure further include generating a risk profile based on a history of pre-ictal risk indicators associated with the user.

Embodiments of the present disclosure further include generating treatment plan optimizations for mitigating seizures.

Embodiments of the present disclosure further include generating a seizure mitigation suggestion based on the pre-ictal risk indicator and the at least one data stream.

Embodiments of the present disclosure further include where the seizure mitigation suggestion includes one or more of: i) a medication administration, ii) a release of stimulation, or iii) a combination thereof.

Embodiments of the present disclosure further include communicating with a wearable device to receive the at least one data stream in real-time.

Embodiments of the present disclosure further include where the wearable device includes a wrist worn sensor.

Embodiments of the present disclosure further include where the at least one data stream includes: i) electrodermal activity, ii) heart rate, iii) blood volume pulse, iv) temperature, v) accelerometer-based movement data, vi) electroencephalogram measurements, vii) time, viii) date, ix) global positioning system data, x) medication, xi) self-reported seizures, xii) other clinical and medical record data and characteristics or xiii) combinations thereof.

Embodiments of the present disclosure further include where the time segment used to calculate forecasts includes thirty seconds.

Embodiments of the present disclosure further include where the integration window includes a rolling three hundred second period of the history of pre-ictal period probabilities.

Embodiments of the present disclosure further include determining an inter-ictal period upon the pre-ictal period probability falling below the pre-ictal probability threshold.

Embodiments of the present disclosure further include maintaining an alert status associated with the pre-ictal alert until a seizure occurrence period has passed.

Embodiments of the present disclosure further include modifying a time-span of the integration window, a time span of the forecasted time segment (i.e. the seizure occurrence period), the pre-ictal probability threshold, or combinations thereof, based on an accuracy of the pre-ictal risk alert for the user.

Definitions

Throughout the specification, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments may be readily combined, without departing from the scope or spirit of the present disclosure.

As used herein, the term "data stream" refers to a periodic or continuous transmission of data from one system, device, or component to another via any suitable wired or wireless data communication devices and techniques.

As used herein, the term "tonic clonic seizure" refers to a type of seizure, also known as a grand mal seizure, characterized by a tonic phase where the body becomes rigid, followed by a clonic phased where the body undergoes uncontrolled jerking.

As used herein, the term "ictal" refers to the period a physiologic state or event such as a seizure, and may be used to further indicate the period of a, e.g., stroke, headache, inflammation, flare-up, mental health episode, or in general any relapsing-remitting diseases.

As used herein, the term "preictal" refers to the time period preceding an ictal event of variable duration.

As used herein, the term "interictal" refers to the period between ictal events.

As used herein, the term "postictal" refers to the period refers to the state shortly after an ictal event.

As used herein, the term "periictal" refers to the period encompassing preictal, ictal and postictal periods.

As used herein, the term "electrodermal activity" refers to a measure of neurally mediated effects on sweat gland permeability, observed as changes in the resistance of the skin to a small electrical current, or as differences in the electrical potential between different parts of the skin.

As used herein, the term "integration window" refers to a time period including data on which an operation is to be performed.

As used herein, the term "ground-truth" refers to one or more sets of object, provable data.

As used herein, the term "multi-modal" refers to the statistical distribution of values with multiple peaks.

As used herein, the term "electroencephalography (EEG)" refers to the measurement of electrical activity in different parts of the brain.

As used herein, the term "electrocorticography (ECoG)" refers to e direct recording of electrical potentials associated with brain activity from the cerebral cortex.

As used herein, the term "electrocardiography (ECG)" refers to the measurement of electrical activity in the heart using electrodes placed on the skin of the limbs and chest.

As used herein, the term "biosensor" refers to a device configured to and/or capable of producing data streams of clinical, biological or physiological parameters by sensing such parameters from a patient.

As used herein, the term "sensitivity" refers to the true positive seizure prediction rate.

As used herein, the term "time in warning" refers to the fraction of time spent in warning.

As used herein, the term "improvement over chance" refers to the difference between sensitivity and time in warning.

As used herein, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, the term "real-time" is directed to an event/action that can occur instantaneously or almost instantaneously in time when another event/action has occurred. For example, the "real-time processing," "real-time computation," and "real-time execution" all pertain to the performance of a computation during the actual time that the related physical process (e.g., a user interacting with an application on a mobile device) occurs, in order that results of the computation can be used in guiding the physical process.

As used herein, the term "dynamically" and term "automatically," and their logical and/or linguistic relatives and/or derivatives, mean that certain events and/or actions can be triggered and/or occur without any human intervention. In some embodiments, events and/or actions in accordance with the present disclosure can be in real-time and/or based on a predetermined periodicity of at least one of: nanosecond, several nanoseconds, millisecond, several milliseconds, second, several seconds, minute, several minutes, hourly, several hours, daily, several days, weekly, monthly, etc. It is understood that at least one aspect or functionality of various embodiments described herein can be performed in real-time or dynamically, or both.

As used herein, the terms "computer engine" and "engine" identify at least one software component and/or a combination of at least one software component and at least one hardware component which are designed, programmed or otherwise configured to manage or control other software and hardware components (such as the libraries, software development kits (SDKs), objects, etc.).

As used herein, term "server" should be understood to refer to a service point which provides processing, database, and communication facilities. By way of example, and not limitation, the term "server" can refer to a single, physical processor with associated communications and data storage and database facilities, or it can refer to a networked or clustered complex of processors and associated network and storage devices, as well as operating software and one or more database systems and application software that support the services provided by the server. Cloud servers are examples.

As used herein, the term "mobile electronic device," or the like, may refer to any portable electronic device that may or may not be enabled with location tracking functionality (e.g., MAC address, Internet Protocol (IP) address, or the like). For example, a mobile electronic device can include, but is not limited to, a mobile phone, Personal Digital Assistant (PDA), Blackberry™, Pager, Smartphone, or any other reasonable mobile electronic device.

As used herein, terms "proximity detection," "locating," "location data," "location information," and "location tracking" refer to any form of location tracking technology or locating method that can be used to provide a location of, for example, a particular computing device, system or platform of the present disclosure and any associated computing devices, based at least in part on one or more of the following techniques and devices, without limitation: accelerometer(s), gyroscope(s), Global Positioning Systems (GPS); GPS accessed using Bluetooth™; GPS accessed using any reasonable form of wireless and non-wireless communication; WiFi™ server location data; Bluetooth™ based location data; triangulation such as, but not limited to, network based triangulation, WiFi™ server information based triangulation, Bluetooth™ server information based triangulation; Cell Identification based triangulation, Enhanced Cell Identification based triangulation, Uplink-Time difference of arrival (U-TDOA) based triangulation, Time of arrival (TOA) based triangulation, Angle of arrival (AOA) based triangulation; techniques and systems using a geographic coordinate system such as, but not limited to, longitudinal and latitudinal based, geodesic height based, Cartesian coordinates based; Radio Frequency Identification such as, but not limited to, Long range RFID, Short range RFID; using any form of RFID tag such as, but not limited to active RFID tags, passive RFID tags, battery assisted passive RFID tags; or any other reasonable way to determine location. For ease, at times the above variations are not listed or are only partially listed; this is in no way meant to be a limitation.

As used herein, terms "cloud," "Internet cloud," "cloud computing," "cloud architecture," and similar terms correspond to at least one of the following: (1) a large number of computers connected through a real-time communication network (e.g., Internet); (2) providing the ability to run a program or application on many connected computers (e.g., physical machines, virtual machines (VMs)) at the same time; (3) network-based services, which appear to be provided by real server hardware, and are in fact served up by virtual hardware (e.g., virtual servers), simulated by software running on one or more real machines (e.g., allowing to be moved around and scaled up (or down) on the fly without affecting the end user).

As used herein, the term "user" shall have a meaning of at least one user. In some embodiments, the terms "user", "subscriber" "consumer" or "customer" should be understood to refer to a user of an application or applications as described herein and/or a consumer of data supplied by a data provider. By way of example, and not limitation, the terms "user" or "subscriber" can refer to a person who receives data provided by the data or service provider over the Internet in a browser session, or can refer to an automated software application which receives the data and stores or processes the data.

As used herein, the terms "and" and "or" may be used interchangeably to refer to a set of items in both the conjunctive and disjunctive in order to encompass the full description of combinations and alternatives of the items. By way of example, a set of items may be listed with the disjunctive "or", or with the conjunction "and." In either case, the set is to be interpreted as meaning each of the items singularly as alternatives, as well as any combination of the listed items.

BRIEF DESCRIPTION OF THE DRAWINGS

Various embodiments of the present disclosure can be further explained with reference to the attached drawings, wherein like structures are referred to by like numerals throughout the several views. The drawings shown are not necessarily to scale, with emphasis instead generally being placed upon illustrating the principles of the present disclosure. Therefore, specific structural and functional details disclosed herein are not to be interpreted as limiting, but merely as a representative basis for teaching one skilled in the art to variously employ one or more illustrative embodiments. The FIGS. including.

DETAILED DESCRIPTION

Figure 1:
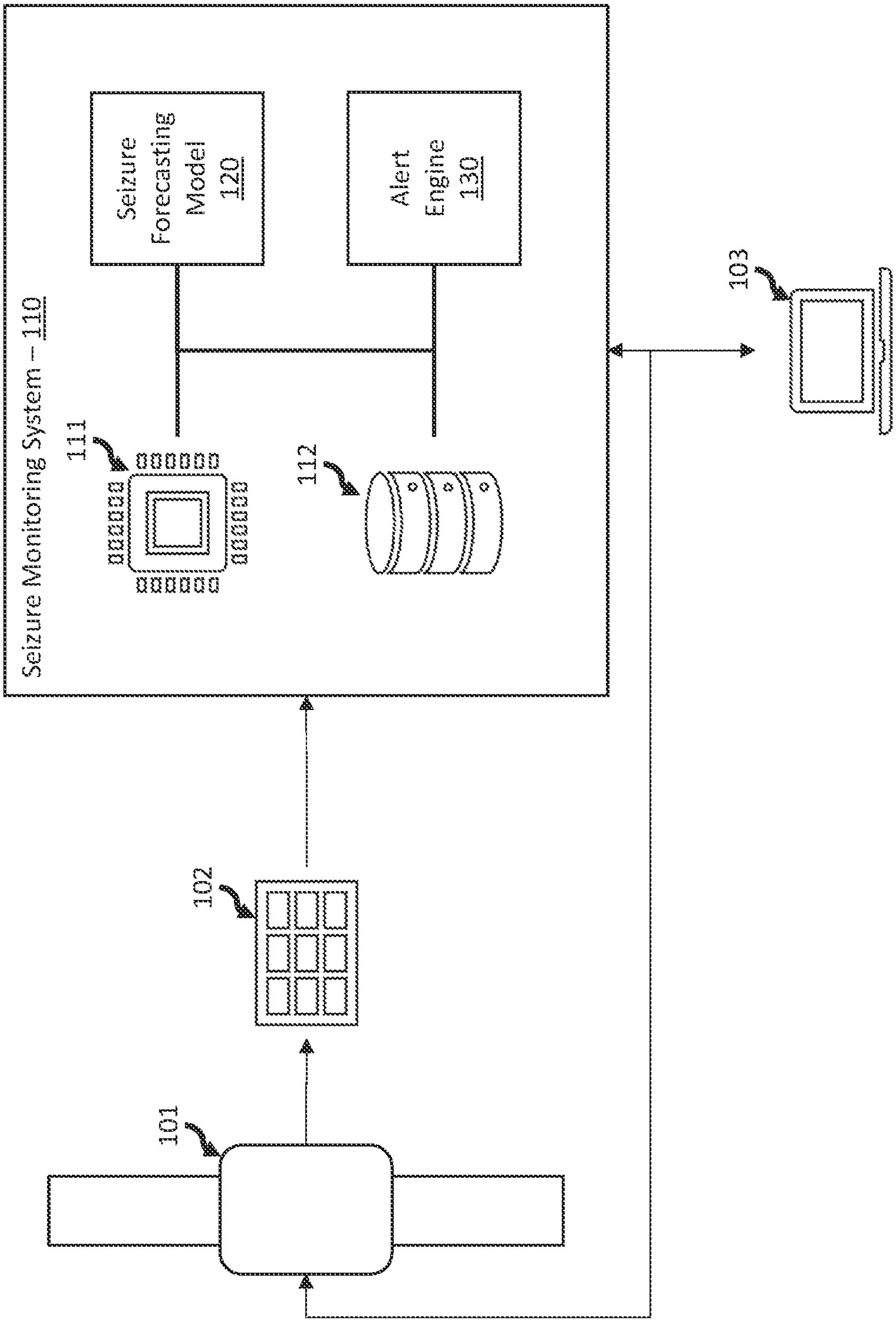
FIG. 1 depicts a block diagram of an exemplary computer-based system and platform for seizure monitoring and seizure risk prediction in accordance with one or more embodiments of the present disclosure.

Various detailed embodiments of the present disclosure, taken in conjunction with the accompanying figures, are disclosed herein; however, it is to be understood that the disclosed embodiments are merely illustrative. In addition, each of the examples given in connection with the various embodiments of the present disclosure is intended to be illustrative, and not restrictive.

In order to make seizure risk assessments available for broader clinical use methods that build on non-invasive, easily recordable data streams and that can be readily used without the need of an adjustment phase or expert parameter setting are desirable. Peripheral signals recorded using wearable devices, such as wearable sensors, are particularly interesting in this respect since these signals permit continuous, non-invasive recording of several physiological parameters, such as electrodermal activity, body temperature, blood volume pulse and actigraphy. At the same time, the compact design may limit the risk of stigmatization, affords more easy application, and may altogether increase patient adherence relevant for long-term ambulatory use. Furthermore, the data streams may also include signals including additional physiological parameters and patient data such as, e.g., heart rate, accelerometer-based movement data, electroencephalogram measurements, time, date, global positioning system data, medication, self-reported seizures, clinical patient data, electronic medical record data, and combinations thereof. Monitoring of such physiological parameters has already been demonstrated to assist in the detection of generalized tonic-clonic seizures. Similar autonomous system measures may also provide information on detection of preictal patterns or periods.

Deep learning has been shown to exhibit strong classification performance from complex feature sets. It therefore constitutes a promising technique to differentiate pre- from interictal periods based on complex, multi-modal wearable sensor data. While more traditional machine learning approaches rely on hand-designed feature sets, deep learning uses multiple layers of connections to perform classification tasks without the need of feature designing, which may be an advantage in relatively under-explored, multi-modal datasets, such as data from wrist-worn devices.

FIGS. 1 through 17 illustrate systems and methods of using neural networks to pre-emptive forecast the occurrence of seizures from sensor data collected from a wearable sensor on a user's body. The following embodiments provide technical solutions and technical improvements that overcome technical problems, drawbacks and/or deficiencies in the technical fields involving seizure analysis and diagnosis, and seizure risk assessment. As explained in more detail, below, technical solutions and technical improvements herein include aspects of data streams continuously collected form wearable sensor devices and neural network models for forecasting seizure risk using the sensor data without the need of feature designing and without the need for EEG, EKG and ECOG tests that are expensive and cumbersome, and can only be performed occasionally a great expense of time and money. Based on such technical features, further technical benefits become available to users and operators of these systems and methods. Moreover, various practical applications of the disclosed technology are also described, which provide further practical benefits to users and operators that are also new and useful improvements in the art.

FIG. 1 illustrates a block diagram of an exemplary computer-based system and platform for seizure monitoring and seizure risk prediction in accordance with one or more embodiments of the present disclosure.

In some embodiments, a seizure monitoring system 110 using wearable sensor data 102 to forecast seizure risks in a user without the need for expensive and cumbersome EEG, EKG and ECOG tests that would ordinarily be used for assessing seizures. The wearable sensor data 102 can be provided to the seizure monitoring system 110 from a wearable sensor 101 as a continuous stream of data. Thus, the seizure monitoring system 110 may monitor the user's sensor data 102 in real-time, thus enabling timely intervention or mitigation of impending seizures using discrete, wearable sensing devices. As a result, the seizure monitoring system 110 uses peripheral signals from a device having a compact, wearable design that may limit the risk of stigmatization, affords more easy application, and may altogether increase patient adherence relevant for long-term ambulatory use, while also providing effective, real-time monitoring beyond the typical occasional and expensive EEG, ECG and ECOG testing.

As such, in some embodiments, the wearable sensor 101 can include any suitable sensing device for sensing physiological parameters. In some embodiments, the wearable sensor 101 can include a device for sensing parameters, such as, e.g., electrodermal activity, body temperature, blood volume pulse, heart rate, heart rate variability, blood oxygen content, blood glucose data, electrocardiographic data and actigraphy (accelerometer-based and location-based activity data), electroencephalogram measurements, time, date, medications, self-reported seizures, and combinations thereof. For example, the wearable sensor 101 can include, e.g., a smartwatch, a wristband sensor, a chest strap, a smart ring, or other health tracking sensor device, and combinations thereof. The wearable sensor data 102 may be continuously collected, e.g., at about 60 hertz (Hz), 30 Hz, 20 Hz, 15 Hz, 10 Hz, 5 Hz, 1 Hz or other sampling rate. Thus, the seizure monitoring system 110 is provided with continuous streams of each physiological parameter in the wearable sensor data 102.

In some embodiments, the seizure monitoring system 110 may receive the wearable sensor data 102 as a continuous data stream of each of the physiological parameters. In some embodiments, the seizure monitoring system 110 may use a combination of software and hardware components to record and process the data to forecast a risk of the user experiencing a seizure and generate an alert to the user indicating the risk.

Examples of software components may include programs, applications, operating system software, middleware, firmware, software modules, routines, subroutines, functions, methods, procedures, software interfaces, application program interfaces (API), instruction sets, computer code, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

Examples of hardware components may include processors 111, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

In some embodiments, the hardware components may also include a data storage 112. In some embodiments, the data storage 112 may include, e.g., a suitable memory or storage solutions for providing electronic data to the seizure monitoring system 110. For example, the data storage 112 may include, e.g., a centralized or distributed database, cloud storage platform, decentralized system, server or server system, among other storage systems, or the data storage 112 may include, e.g., a hard drive, solid-state drive, flash drive, or other suitable storage device, or the data storage 112 may include, e.g., a random access memory, cache, buffer, or other suitable memory device, or any other data storage solution and combinations thereof.

In some embodiments, the data storage 112 may receive and record the continuous stream of wearable sensor data 102 among other patient data, including electronic medical record data, clinical data, radiological and other imagery and test results, medication and medication dosages, and any other health-related data, such as any data from an electronic medical health record or other health record. The wearable sensor data 102 may be accessible by, e.g., a seizure forecasting model 120 and an alert engine 130, e.g., via the processor 111. However, in some embodiments, the wearable sensor data 102 may be provided directly to the forecasting model 120 and the alert engine 130 before or instead of being stored in the data storage 112.

In some embodiments, the seizure forecasting model 120 includes a combination of hardware and/or software for predicting seizure risk at a given time based on the wearable sensor data 102, or a subset of the wearable sensor data 102 pertaining to a selected segment of time preceding the given time. In some embodiments, the seizure forecasting model 120 may predict a seizure risk level once every prediction period. In some embodiments, the prediction period may be, e.g., every second, every ten seconds, every fifteen seconds, every twenty seconds, every thirty seconds, every minute, or other suitable period. Thus, for each prediction period, the seizure forecasting model 120 may develop a seizure risk prediction for that prediction period based on the wearable sensor data 102 and other health-related data associated with the prediction period. In some embodiments, the prediction periods are continuous, non-overlapping segments of time including the wearable sensor data 102 during that time.

However, in some embodiments, the prediction periods may overlap, such that the time segment preceding the given time at which a seizure risk prediction is made overlaps with a previous time segment for predicting seizure risk at a previous time. For example, a first 30 second prediction period may include the time segment from t=0 seconds to t=30 seconds for a prediction at t=30 of seizure risk, with a second 30 second prediction period including the time segment from t=15 seconds to t=45 seconds for a prediction at t=45 of seizure risk. Thus, the prediction period may include a moving time window approach that may form predictions based on windows having a size according to the prediction period and move according to, e.g., an update period. In some embodiments, the update period may be any suitable increment of time less than the prediction period.

In some embodiments, the seizure forecasting model 120 may include, e.g., a suitable machine learning algorithm for classifying a seizure risk based on the physiological parameters of the wearable sensor data 102 and health-related data, such as electronic medical record data. The classification of seizure risk can include a period type relative to a seizure, or ictal period. For example, the seizure forecasting model 120 may forecast a seizure risk based on a classification of any given time period as, e.g., preictal, postictal or interictal.

Thus, in some embodiments, the prediction based on the wearable sensor data 102 for a particular prediction period results in a seizure risk forecast including the classification of that the prediction period as preictal, postictal or interictal. However, in some embodiments, since postictal periods follow a seizure event, the predictive power of such periods are low. Thus, the seizure forecasting model 120 may be configured to predict whether a prediction period is preictal or not preictal (e.g., interictal and/or postictal). For example, the seizure forecasting model 120 may be trained to recognize physiological parameters during a time period that would indicate that preictal period correspond to a seizure being imminent within, e.g., about 61 minutes of a current time.

Thus, in some embodiments, the seizure forecasting model 120 may include a machine learning model for differentiating between the periictal periods, and in particular, in distinguishing a preictal period indicating a high risk of an impending seizure, e.g., a high risk of a seizure occurring within a seizure occurrence period, e.g., within about 61 minutes of the high risk indication. In some embodiments, a data segment may be preictal if it occurs between 61 minutes and 1 minute prior to a seizure, thus leaving a one-minute buffer prior to seizure onset. This preictal window definition is commensurate with other seizure forecasting research using EEG and ECoG and may account for potential small ambiguities in determining the exact seizure onset between EEG and wristband. A data segments may classified as interictal or not preictal to indicate that the associated prediction period is two hours or more away from any seizure.

To do so, in some embodiments, the seizure forecasting model 120 may include artificial intelligence (AI) or machine learning techniques for forecasting a preictal period based on wearable sensor data 102 of physiological parameters and physiological data from, e.g., electronic medical health records, the techniques chosen from, but not limited to, decision trees, boosting, support-vector machines, neural networks, nearest neighbor algorithms, Naive Bayes, bagging, random forests, and the like. In some embodiments and, optionally, in combination of any embodiment described above or below, an exemplary neutral network technique may be one of, without limitation, feedforward neural network, radial basis function network, recurrent neural network, convolutional network (e.g., U-net), long short-term memory network or other suitable network. In some embodiments and, optionally, in combination of any embodiment described above or below, an exemplary implementation of Neural Network may be executed as follows:

i) define Neural Network architecture/model,
ii) transfer the input data to the exemplary neural network model,
iii) train the exemplary model incrementally,
iv) determine the accuracy for a specific number of timesteps,
v) apply the exemplary trained model to process the newly-received input data,
vi) optionally and in parallel, continue to train the exemplary trained model with a predetermined periodicity.

In some embodiments and, optionally, in combination of any embodiment described above or below, the exemplary trained neural network model may specify a neural network by at least a neural network topology, a series of activation functions, and connection weights. For example, the topology of a neural network may include a configuration of nodes of the neural network and connections between such nodes. In some embodiments and, optionally, in combination of any embodiment described above or below, the exemplary trained neural network model may also be specified to include other parameters, including but not limited to, bias values, functions and aggregation functions. For example, an activation function of a node may be a step function, sine function, continuous or piecewise linear function, sigmoid function, hyperbolic tangent function, or other type of mathematical function that represents a threshold at which the node is activated. In some embodiments and, optionally, in combination of any embodiment described above or below, the exemplary aggregation function may be a mathematical function that combines (e.g., sum, product, etc.) input signals to the node. In some embodiments and, optionally, in combination of any embodiment described above or below, an output of the exemplary aggregation function may be used as input to the exemplary activation function. In some embodiments and, optionally, in combination of any embodiment described above or below, the bias may be a constant value or function that may be used by the aggregation function and/or the activation function to make the node more or less likely to be activated.

In some embodiments, the classification from the seizure forecasting model 120 can be provided to an alert engine 130 for generating an alert that a seizure event may be imminent based on the prediction period being a preictal period. In some embodiments, the seizure forecasting model 120 may first provide each seizure classification for each prediction period to the data storage 112 to record the prediction period with an indication of the associated classification. In some embodiments, the classification may be provided to the data storage 112, which may then be accessed by the alert engine 130, or the seizure forecasting model 120 may provide the classification directly to the alert engine 130, either before, after or concurrently with recording the classification in the data storage 112.

In some embodiments, the classification from the seizure forecasting model 120 can include a binary classification (e.g., preictal or not preictal). The binary classification can include a probability that a given prediction period is a preictal period based on the wearable sensor data 102. For example, the classification may include a numerical value on a scale from 0 to 1, where 0 indicates a zero percent probability of the prediction period being a preictal period, and where 1 indicates a one hundred percent probability of the prediction period being a preictal period. In practice, any given prediction period is unlikely to be a 0 or a 1, but likely may be classified somewhere in between.

In some embodiments, the alert engine 130 may determine that the probability of the classification indicates a preictal period using, e.g., a risk threshold. For example, where the probability rises above a risk threshold of, e.g., 0.5, 0.52, 0.54, 0.56, 0.58, 0.6, the alert engine 130 may determine that the prediction period is a preictal period, thus indicating that a seizure is imminent within about an hour. Thus, the alert engine 130 may generate an alert to the user. In some embodiments, the probability for each prediction period may be compared to the risk threshold.

However, irregularities may occur at any particular prediction period that may give rise to a high probability of the preictal period classification for one prediction period. Thus, a seizure may only be actually imminent where the physiological parameters consistently indicate a preictal period according to the associated classification probabilities. Therefore, in some embodiments, an integration window may be employed where the preictal classification probabilities for each prediction period within a windowed time span may be aggregated and then compared to the risk threshold. For example, the integration window may encompass a time span including, e.g., 90, 120, 150, 300, 600, or 1200 seconds.

In some embodiments, the alert generator 130 may generate an alert including, e.g., a visual indication via a graphical user interface, an audible indication, a vibration or tactile indication, or other alert notifying the user of the risk of a seizure based on the preictal classification. In some embodiments, the alert may be provided to a user computing device 103 or to the wearable sensor 101, or both. In some embodiments, the user computing device 103 may include, e.g., a personal computer, mobile device, wearable device, tablet computer, or other computing device associated with the user. For example, the user computing device 103 and/or the wearable sensor 101 may display the visual indication and/or emit the audible, vibration and/or tactile indication such that the user may perceive the alert of the risk of an imminent seizure. As a result, the user may receive a real-time warning for imminent seizures, enabling the user to take preventative or mitigating steps to avoid harm that may result from a seizure. Similarly, the user may receive a real-time indication that seizure risk is low, a real-time indication of the current seizure risk at any time, or other real-time seizure risk indication techniques. The alert generator 130 may also be configured to determine a mitigation or treatment strategy along with the alert, such as, e.g., a notification to stop a car, lie down, ingest a prescribed medication, etc. The alert generator 130 may also be embedded in a closed-loop setup linked to a device to administer treatment and thereby lower the risk of a seizure or prevent it completely. This treatment device may include a system to apply a fast-acting antiseizure medication or a neuromodulatory device which, for example, administers electrical stimulation to the brain in order to decrease seizure risk.

Figure 2:
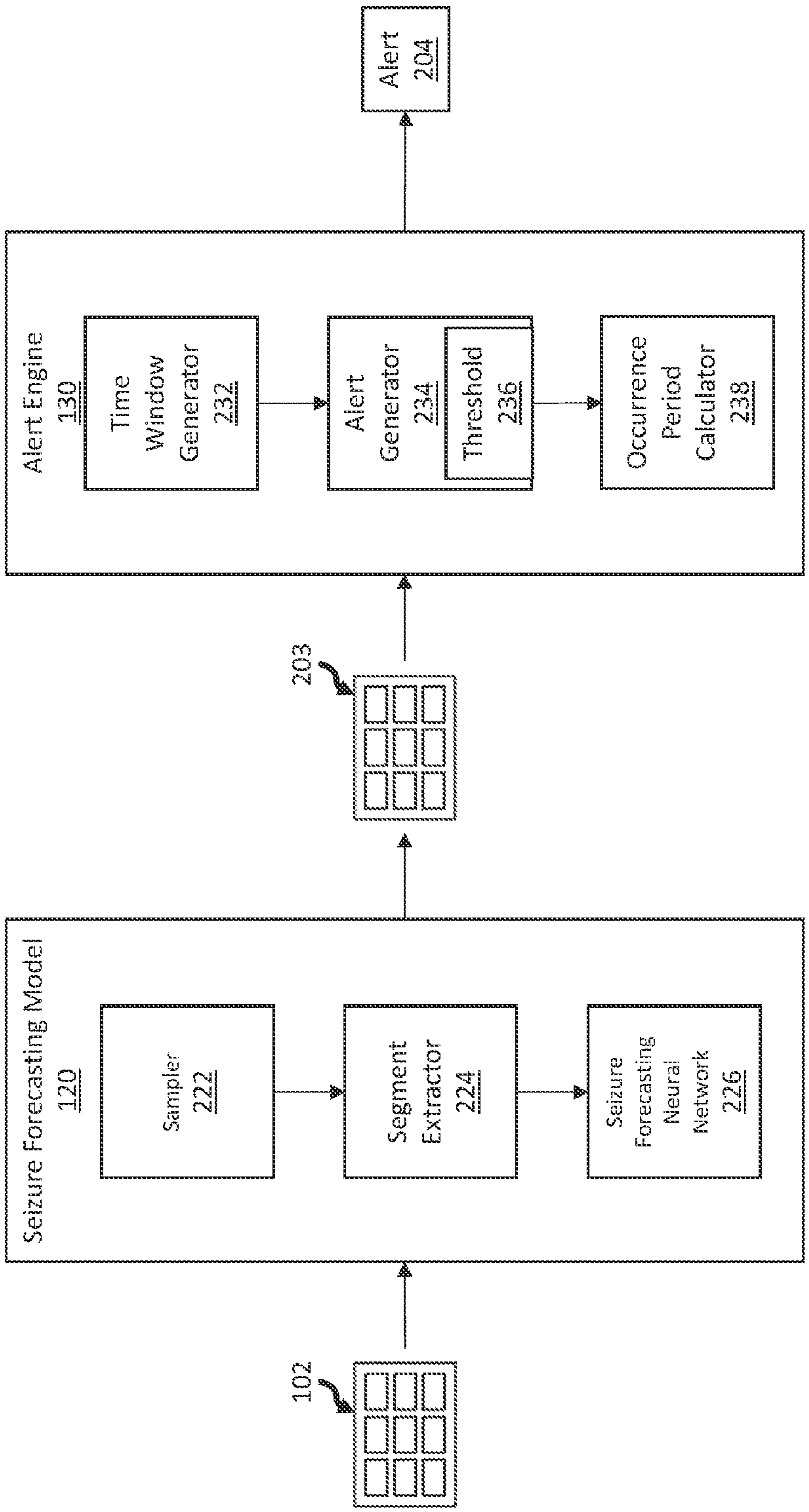
FIG. 2 depicts a block diagram of another exemplary computer-based system and platform including a seizure forecasting model and windowing engine for seizure monitoring and seizure risk prediction in accordance with one or more embodiments of the present disclosure.

FIG. 2 illustrates a block diagram of another exemplary computer-based system and platform including a seizure forecasting model and windowing engine for seizure monitoring and seizure risk prediction in accordance with one or more embodiments of the present disclosure.

In some embodiments, seizure forecasting builds on the notion that a preictal period, during which a seizure is more likely to occur soon, can be reliably distinguished from interictal periods. However, previous studies have focused on data recorded either from ECoG and EEG or from ECG. ECG has thus been a long-standing example that peri- and preictal changes can not only be detected within the central nervous system but are also reflected in a variety of cardiac effects. Cardiac activity is controlled by parasympathetic and sympathetic branches of the autonomic nervous system, with the former producing an inhibitory response and the latter producing an excitatory response on heart rate. Preictal changes in brain activity that occur in or propagate to autonomic control centers may affect this autonomic balance and, consequently, affect cardiac activity during the leadup to a seizure.

In some embodiments, it is assumed that single-channel ECG contains a comparable amount of information to multichannel EEG. Therefore, peripheral sensors, such as the wearable sensor 101 may be relevant for seizure forecasting. In some embodiments, autonomous nervous system changes are correlated to the wristband sensor data 102 in several ways: electrodermal activity is known to be sensitive to sympathetic innervation; blood volume pulse curves contain information about heartrate which is controlled by the parasympathetic and sympathetic interplay; and body temperature is similarly known to be maintained by the autonomic nervous system. In some embodiments, the peripheral biomarker parameters are built on by monitoring both these autonomous nervous system functions along with actigraphy, which indirectly also monitors resting periods and sleep. Thus, in some embodiments, the seizure forecasting model 120 and alert engine 130 are configured to leverage such multi-modal wearable sensor data 102, going beyond more traditional ECoG/EEG and ECG approaches to enable real-time, ever-present seizure monitoring to warn users of impending seizures.

In particular, in some embodiments, the seizure forecasting model 120 receives the multi-modal wearable sensor data 102 and analyzes the data with a sampler 222, segment extractor 224 and seizure forecasting neural network 226 to predict a seizure risk according to the inferences described above correlating multimodal peripheral biomarker data to preictal period signatures.

In some embodiments, the seizure forecasting model 120 employs the sampler 222 to standardize and down-sample the wearable sensor data 102 streams of each parameter to standardize data vector lengths. For example, as described above, the parameters may include, e.g., blood volume pulse, electrodermal activity, body temperature, and actigraphy. In some embodiments, the actigraphy includes accelerometer based body movement data, including x-axis acceleration measurement, y-axis acceleration measurement and z-axis acceleration measurements. Thus, the wearable sensor data 102 may include six data streams including a blood volume pulse data stream, an electrodermal activity data stream, a body temperature data stream, an x-axis acceleration data stream, a y-axis acceleration data stream and a z-axis acceleration data stream. However, not all of these data streams may collect data at the same sample rate. Thus, the sampler 222 may down-sample all data streams to a sample rate associated with the lowest sample rate of the data streams. However, the data streams may be down-sampled further to, e.g., reduce unnecessary data, thus improving efficiency. Moreover, a lower data stream may reduce overfitting of the seizure forecasting neural network 226 upon optimization. In some embodiments, the sampler 222 is configured to downsample the data streams of the wearable sensor data 102 to, e.g., between about 2 Hz and about 10 Hz, and may be about 4 Hz.

Moreover, the sampler 222 may also sample other medical and clinical data pertaining to the wearer of the wearable sensor device 101. For example, the sampler 222 may sample, e.g., test results, medication and medication dosages, EEG data, ECoG data, diagnoses, genetic information such as gene presence and gene expression, among other information. While some of medical and clinical data may be static between visits with a doctor or clinician, the sampler 222 may convert parameters of the medical and clinical data as a continuous data stream, e.g., as a 4 Hz continuous signal similar to the sampled wearable sensor data 102 by representing a data point as a constant value signal between each change. For example, where a patient is given a particular dosage of a particular medication, a signal representing the dosage of the medication may be employed as a constant value four times per second (e.g., for a 4 Hz sample rate) until a clinician or doctor prescribes a new dosage or new medication, or both. Thus, each medical parameter of the medical and clinical data may be represented as a time-series for ease of used alongside the wearable sensor data 102.

In some embodiments, the sampler 222 may filter and/or down-sample the wearable sensor data 102 and medical and clinical data streams in real-time as it is received by the seizure forecasting model 120. The filtered and/or down-sampled data may then be extracted in time segments based on the prediction period described above. As such, the segment extractor 224 may receive the filtered and/or down-sampled data streams and extract overlapping or non-overlapping continuous segments of data from each data stream, where each segment includes the data within the prediction period, e.g., about 30 seconds. As a result, the segment extractor 224 may generate a series of, e.g., 30 second segments of 4 Hz data streams (about 120 data points) from each of the six data streams associated with the six peripheral biomarker parameters.

In some embodiments, the segment extractor 224 may extract the time segments of data from the data streams in the wearable sensor data 102 before the data streams are sampled by the sampler 222. Thus, the original data streams may have segments extracted therefrom, and then the sampler 222 may downsample the data segments. Where overlapping segments are employed, such an approach may result in increased computation by down-sampling the overlapping portions of segments more than once. However, accuracy and effectiveness may nevertheless be comparable.

In some embodiments, the segments of down-sampled data streams are received by the seizure forecasting neural network 226 to classify each segment according to a probability of being within a preictal period. In some embodiments, there exists a preictal signature in autonomous nervous system and actigraphy data, which, despite possibly not being detectable by visual inspection, may be picked up by deep learning. This signature may be learned across patients and is therefore not patient-specific. This is an advance from most traditional seizure prediction work, which mostly succeeded when using algorithms designed specifically for each individual patient. An algorithm that can be trained across patients has the advantage that it can be readily employed to a new patient, without any training to learn patient-specific factors or expert knowledge to set parameters.

In some embodiments, the deep learning used to form the non-patient-specific algorithm may be a suitable classification algorithm with robust classification performance based on multi-dimensional timeseries data, while being resistant to overfitting. For example, a network of long short-term memory (LSTM) units or neurons may be employed. In some embodiments, to limit LSTMs from overfitting, network architecture was kept simple and shallow. For example, the LSTM network may employ, e.g., about 20 or fewer nodes, or about 10 or fewer nodes with a dropout rate between about, e.g., 0.4 and 0.6 and a recurrent dropout rate between about, e.g., 0.4 and 0.6. Thus, an LSTM based seizure forecasting neural network 226 may be configured according to Table 1 below:

TABLE 1

| Layer number | Layer type | Nodes/units | Layer parameters |
|---|---|---|---|
| 1 | LSTM | 10 | dropout rate = 0.5, recurrent dropout rate = 0.5 |
| 2 | Dense | 10 | |
| 3 | Dropout | N/A | dropout rate = 0.7 |
| 4 | Dense | 1 | activation = sigmoid |

However, in some embodiments, 1-dimensional convolutional neural networks (1DConv) may also or alternatively be employed due to their good performance on timeseries data while often being easier and faster to train than LSTM networks. Thus, in some embodiments, the seizure forecasting neural network 226 may employ a 1DConv, for example, with a network of about, e.g., 100 or fewer nodes, or about 81 or fewer nodes, or about 64 or fewer nodes, and about, e.g., 2, 3, 4, or 5 units. In some embodiments, the 1DConv may employ any suitable activation function, such as, e.g., a sigmoid function, a tanh function, rectified linear units (ReLu), leaky ReLu, a maxout function, exponential linear units (ELU), or other activation function. For example, the seizure forecasting neural network 226 may employ a 1DConv as set forth in Table 2 below:

TABLE 2

| Layer number | Layer type | Nodes/units | Layer parameters |
|---|---|---|---|
| 1 | Conv1D | 64/2 | activation = ReLu |
| 2 | MaxPooling1D | 2 | N/A |
| 3 | Dropout | N/A | dropout rate = 0.7 |
| 4 | Dense | 50 | activation = ReLu |
| 5 | Dropout | N/A | dropout rate = 0.7 |
| 6 | Dense | 1 | |

In our approach, the same seizure forecasting neural network 226 may be employed for all users. In some embodiments, the seizure forecasting neural network 226 may be trained separately for each user, however, in some embodiments, the seizure forecasting neural network 226 is trained on a pool of training patients and then used for individual users. In some embodiment, the seizure forecasting neural network 226 may be trained initially on all patients and the further specified to the individual patient by additional training on the individual patient's data. While it is possible that model hyperparameters may be individualized for each patient, which may bring about better performance, the same model architecture may nevertheless be employed across patients to facilitate an "out-of-the-box" solution for future prospective settings and users.

In some embodiments, the seizure forecasting neural network 226 ingests each time segment of down-sampled wearable sensor data and generates a preictal probability 203 of each time segment being part of a preictal period, e.g., on a scale from 0 to 1, as described above. However, to increase the usability of the preictal probabilities 203, the alert engine 130 utilizes the preictal probabilities 203 to alert a user when the user is likely in a preictal period, thus warning the user of an impending seizure.

In some embodiments, the alert engine 130 employs a sliding window approach in which the individual 30-second segment preictal predictions are statistically aggregated over an integration window. If this statistically aggregated value crosses a risk threshold, an alarm may be initiated which may last for the duration of a seizure occurrence period. Thus, in some embodiments, a new alarm may only be initiated once the seizure occurrence period has passed. This post-processing thus employs three additional variables: integration window, threshold and seizure occurrence period. In long-term recordings, parameters like this can in principle be optimized at the individual patient level, for example by optimizing these parameters during an initial adjustment phase. However, in some embodiments, these parameters may be determined, e.g., using a grid search of training data for the parameters yield a greatest improvement-over-chance (IoC) (for example, see, FIG. 12 with integration window values: 150, 300, 600, 1200 seconds; seizure occurrence period values: 150, 300, 600, 1200, 2400, 3600, 7200 seconds; threshold values: 0.5, 0.52, 0.54, 0.56, 0.58, 0.6). In some embodiments, these parameters can be further optimized for the individual patient, for example by determining these parameters during an initial training period or to tune sensitivity versus time in warning to suit the individual patient's needs.

Accordingly, in some embodiments, the preictal predictions 203 may be received by the time window generator 232 to implement the integration window. As such, the time window generator 232 may generate a super-segment of all time segment data and the associated preictal predictions 203 within the period of the integration window. For example, where the integration window value is 600 seconds, the time window generator 232 may identify all of the time segments of wearable sensor data 102 within a 600 second time span and generate a time window of preictal predictions 203 associated with the time segments to compile all preictal predictions 203 within the time window.

In some embodiments, the time window generator 232 compiles preictal predictions 203 in a rolling time window fashion, continuously updating the set of preictal predictions 203 to update the time windowing of preictal predictions 203 with each new preictal prediction. However, other time windowing techniques may be employed.

In some embodiments, the alert generator 234 may statistically aggregate the preictal predictions 203 of each time window of preictal predictions 203 as described above to generate a time window preictal prediction value. In some embodiments, the statistical aggregation may include an averaging of all preictal predictions 203 within the time window. However, in some embodiments, the preictal predictions 203 in a time window may be summed or the segment median may be determined, a weighted average or other statistical operation may be performed, or the individual preictal predictions 203 in the time window may be integrated in a weighted manner, for example, using leaky-integrate-and-fire neural networks, among other aggregation techniques to form a value representing the segment of preictal predictions 203 of the time-window.

In some embodiments, the alert generator 234 may determine whether the time window is a likely to be a preictal period by comparing the time window preictal prediction value with the threshold 236. As described above, the threshold 236 may be, e.g., about 0.50, 0.52, 0.54, 0.56, 0.58, 0.60 or other suitable threshold. In some embodiments, the threshold 236 may be about 0.54. Thus, where the time window preictal prediction value exceeds the threshold 236 of 0.54, the alert generator 234 may determine that the time window corresponds to a preictal period and generate an impending seizure alert 204. In some embodiments, the impending seizure alert 204 may be provided as, e.g., an audible, visual, and/or tactile indication at a user's device (e.g., the wearable sensor 101 or a user computing device 103, as described above), such that the user may be quickly and effectively warned of impending seizures in real-time.

However, continually receiving alerts 204 with every new preictal prediction 203 as the alert engine 130 updates may be annoying and even harmful when a seizure may be imminent. Thus, the occurrence period calculator 238 may utilize the above described occurrence period to prevent new alerts 204 until after the occurrence period has passed. This is because once the user is in a preictal period, each successive prediction period resulting in an additional preictal prediction is likely to indicate a continuation of the preictal period until after the seizure has occurred. Thus, based on the optimal occurrence period identified above, further alerts 204 can be prevented until the occurrence period calculator 238 determines that the seizure occurrence has passed.

Accordingly, in some embodiments, the time at which the alert 204 is generated may be logged by the occurrence period calculator 238 and a timer may be started. The timer may run until the end of the occurrence period. During the occurrence period prior to the end of the timer, the occurrence period calculator 238 may prevent the alert generator 234 from generating new alerts. In some embodiments, the occurrence period calculator 238 may even prevent the alert engine 130 in general from updating with new preictal predictions 203. However, in some embodiments, the time window generator 232 may continue to receive new preictal predictions 204 for rolling the integration window. The alert generator 234 may also continue to statistically aggregate the preictal predictions of the updated time window and, e.g., rescind the alert 204 when the statistical aggregation falls below the threshold 236.

In some embodiments, one may tune the integration window, threshold, and occurrence period parameters for an individual user's needs, for example during an initial adjustment phase, for optimal future performance and patient preferences.

Figure 3:
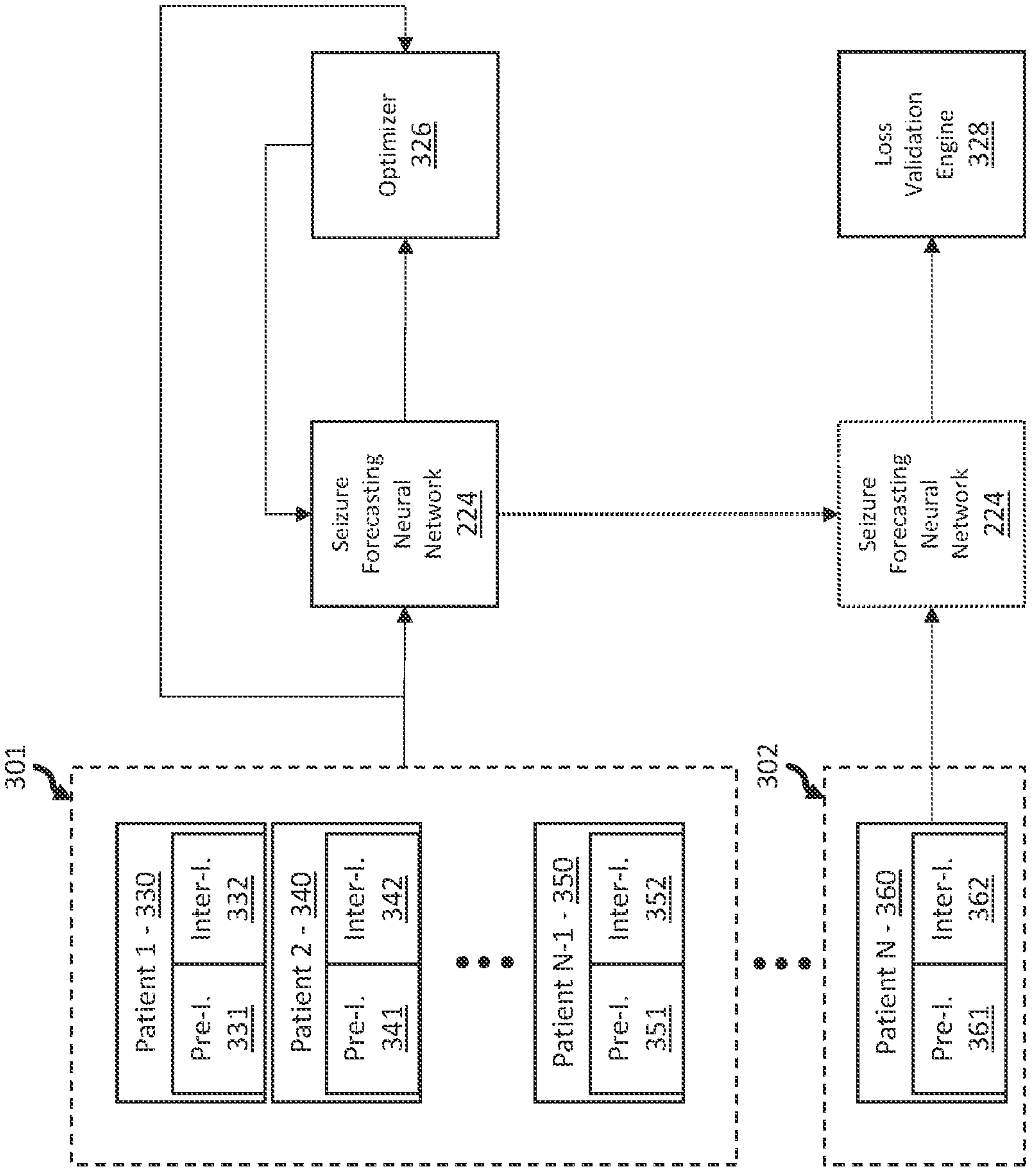
FIG. 3 depicts a block diagram of another exemplary computer-based system and platform including seizure forecasting neural network training and validation for seizure monitoring and seizure risk prediction in accordance with one or more embodiments of the present disclosure.
Figure 4:
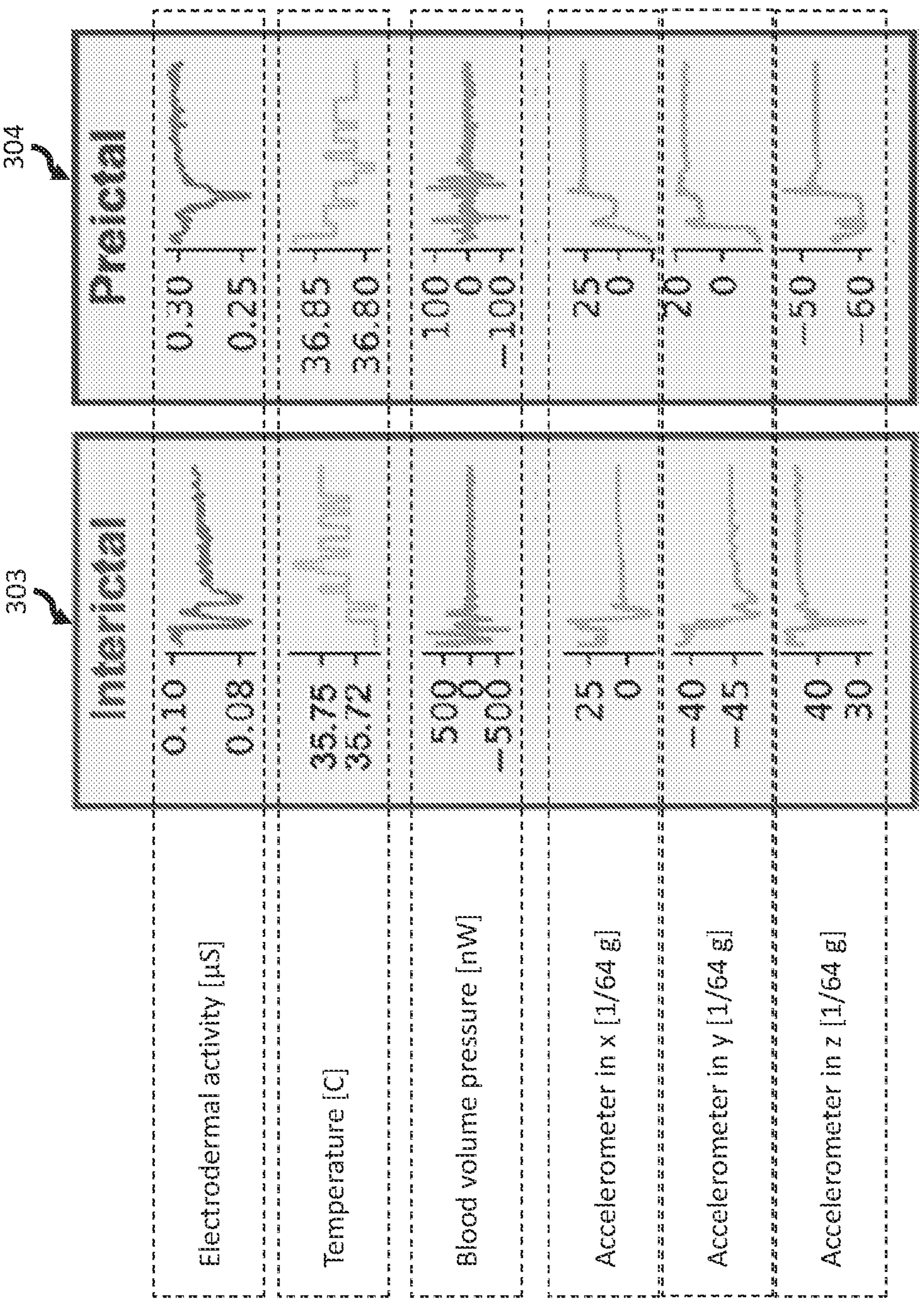
FIG. 4 depicts an outline of data processing for seizure forecasting including a continuous multi-modal timeseries data were separated into consecutive 30-second segments for each of six peripheral biomarker parameters collected by a wearable sensor device, classified according to interictal and preictal signatures in accordance with one or more embodiments of the present invention.
Figure 5:
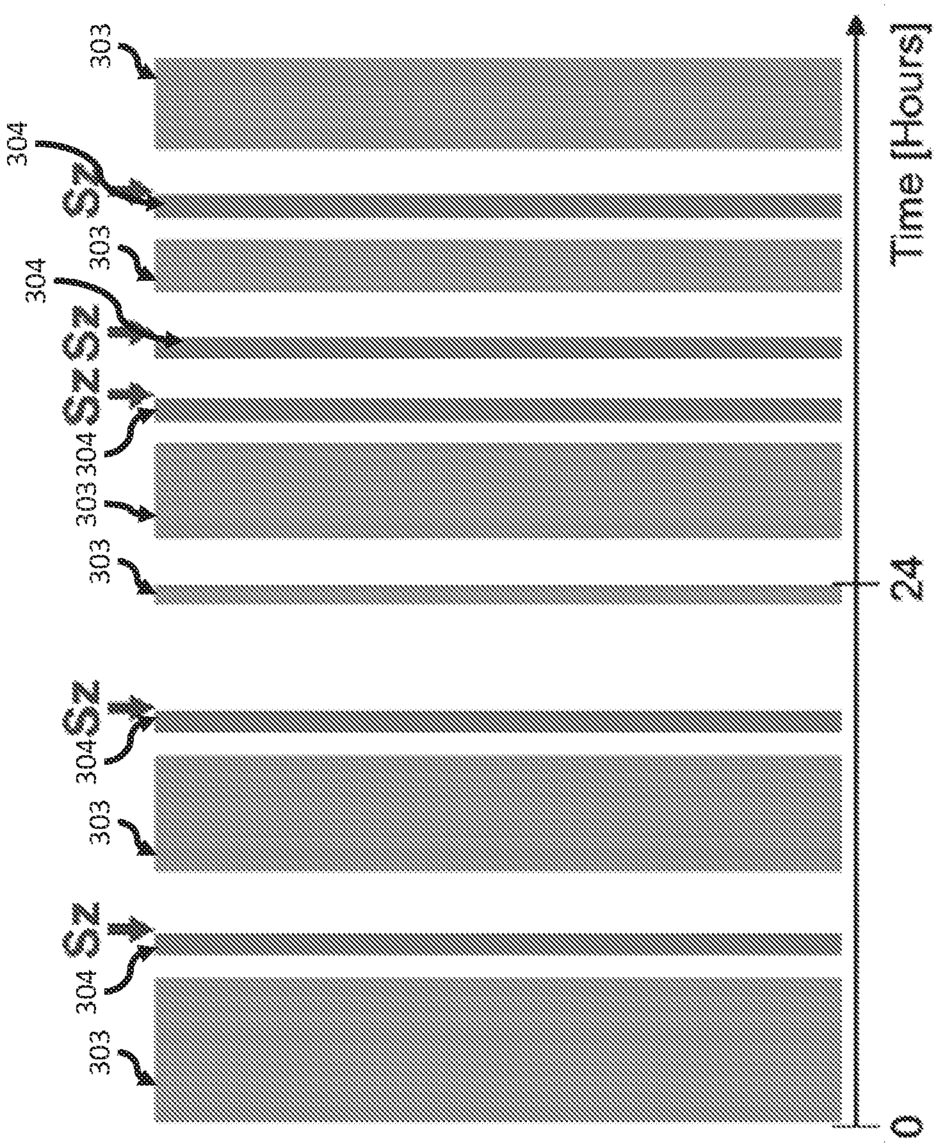
FIG. 5 depicts an outline of data processing for seizure forecasting including data segments in training data were labeled either preictal or interictal in accordance with one or more embodiments of the present invention.

FIG. 3 illustrates a block diagram of another exemplary computer-based system and platform including seizure forecasting neural network training and validation for seizure monitoring and seizure risk prediction in accordance with one or more embodiments of the present disclosure.

Example 1—Training an LSTM-Based Seizure Forecasting Model

Data Recording and Preprocessing

In some embodiments, patients 301 and 302 with epilepsy were selected for training the seizure forecasting neural network 224 and admitted to long-term video-EEG monitoring (LTM) unit and fit with a biosensor wristband on either left or right wrist or ankle for long-term recording. In this example, all patients with wristband recordings were considered from February 2015 until October 2018. Data from one wristband per patient only was considered; when a patient recording involved multiple wristbands (e.g. from wrist and ankle), the data from the biosensor wristband with the longest total recording time was selected for further analysis. From all the patients monitored by wristband recording (about 317 patient), only the patients with at least one seizure during the wristband recording period were included, limiting the analysis to 69 patients (see, for example Table 3 below).

TABLE 3

| Patient | Gender | Age [Years] | Age of First Seizure [Years] | Seizure Types | MRI Findings | Etiology | Wristband Location |
|---|---|---|---|---|---|---|---|
| 1 | male | 15 | 13 | focal onset | not noted | structural | left wrist |
| 2 | male | 13 | 0 | focal onset | normal | unknown | left ankle |
| 3 | female | 17 | unknown | focal onset | normal | unknown | left wrist |
| 4 | female | 2 | unknown | focal onset | volume loss, unspecified | structural | left ankle |
| 5 | female | 5 | 4 | unclassified | malformation | structural | left wrist |
| 6 | female | 15 | 3 | generalized onset, unclassified | gliosis, unspecified | structural | right wrist |
| 7 | female | 22 | 10 | focal onset | infarction | structural | right ankle |
| 8 | female | 16 | 15 | focal onset | normal | unknown | left ankle |
| 9 | male | 17 | 7 | focal onset | normal | unknown | right wrist |
| 10 | male | 3 | 2 | focal onset | dysplasia | structural | right ankle |
| 11 | female | 14 | unknown | generalized onset | cyst | unknown | left wrist |
| 12 | male | 11 | 1 | focal onset | normal | unknown | left wrist |
| 13 | male | 10 | 1 | focal onset | malformation | structural | right wrist |
| 14 | female | 13 | 11 | focal onset, unclassified | volume loss, unspecified | structural | left wrist |
| 15 | male | 16 | 10 | focal onset | normal | unknown | left wrist |
| 16 | male | 8 | 7 | generalized onset | normal | unknown | left ankle |
| 17 | female | 2 | unknown | focal onset, unclassified | tuberous sclerosis/hamartoma | genetic | left ankle |
| 18 | male | 9 | 1 | focal onset, generalized onset | not noted | unknown | right ankle |
| 19 | male | 10 | 8 | focal onset | volume loss, unspecified | unknown | right wrist |
| 20 | male | 9 | 5 | focal onset, generalized onset | normal | unknown | left ankle |
| 21 | male | 5 | 0 | generalized onset | normal | unknown | left wrist |
| 22 | female | 14 | 7 | focal onset | infarction | structural | right wrist |
| 23 | female | 15 | 13 | focal onset, generalized onset | volume loss, unspecified | genetic | left ankle |
| 24 | female | 3 | 0 | generalized onset, unclassified | resection | structural | right ankle |
| 25 | male | 13 | 0 | focal onset | tuberous sclerosis/hamartoma | genetic | right ankle |
| 26 | male | 0 | 0 | focal onset | malformation | structural | right ankle |
| 27 | female | 27 | 14 | generalized onset | normal | unknown | right wrist |
| 28 | male | 17 | 15 | focal onset | tumor | structural | right ankle |
| 29 | male | 13 | 0 | focal onset | resection | unknown | left wrist |
| 30 | female | 2 | 1 | generalized onset | not noted | unknown | right ankle |
| 31 | male | 8 | 1 | focal onset | volume loss, unspecified | structural | right wrist |
| 32 | female | 15 | 0 | focal onset, unclassified | hippocampal sclerosis | structural | right ankle |
| 33 | male | 7 | 4 | focal onset | infarction | structural | left wrist |
| 34 | female | 17 | 1 | generalized onset | not noted | unknown | right wrist |
| 35 | female | 3 | unknown | focal onset | volume loss, unspecified | structural | right ankle |
| 36 | female | 6 | 3 | generalized onset, unclassified | gliosis, unspecified | structural | left wrist |
| 37 | male | 1 | 0 | generalized onset | not noted | unknown | left ankle |
| 38 | female | 11 | 7 | generalized onset | normal | unknown | right wrist |
| 39 | male | 12 | 6 | generalized onset | volume loss, unspecified | structural | right wrist |
| 40 | male | 7 | unknown | generalized onset | volume loss. unspecified | metabolic | right ankle |
| 41 | male | 3 | 1 | focal onset | resection | structural | right wrist |
| 42 | female | 10 | 1 | focal onset, unclassified | dysplasia | structural | right wrist |
| 43 | female | 13 | 0 | focal onset | infarction | structural | left wrist |
| 44 | male | 2 | 0 | generalized onset, unclassified | tuberous sclerosis/hamartoma | genetic | left ankle |

TABLE 3-continued

| Patient | Gender | Age [Years] | Age of First Seizure [Years] | Seizure Types | MRI Findings | Etiology | Wristband Location |
|---|---|---|---|---|---|---|---|
| 45 | male | 4 | 2 | focal onset | volume loss, unspecified | structural | left ankle |
| 46 | female | 5 | 0 | focal onset | infarction | structural | right ankle |
| 47 | male | 8 | 5 | focal onset | tumor | structural | right ankle |
| 48 | female | 13 | 9 | focal onset, unclassified | normal | unknown | left ankle |
| 49 | male | 12 | 7 | focal onset | normal | unknown | right wrist |
| 50 | male | 0 | 0 | generalized onset, unclassified | not noted | unknown | right ankle |
| 51 | male | 9 | unknown | generalized onset | normal | unknown | right wrist |
| 52 | female | 13 | 3 | focal onset | volume loss, unspecified | structural | right wrist |
| 53 | female | 11 | 1 | focal onset | hippocampal sclerosis | structural | right ankle |
| 54 | male | 1 | unknown | focal onset | dysplasia | structural | left ankle |
| 55 | male | 14 | 0 | focal onset, unclassified | resection | structural | left wrist |
| 56 | female | 11 | 10 | generalized onset | tumor | structural | right wrist |
| 57 | female | 19 | 0 | generalized onset | volume loss, unspecified | unknown | right ankle |
| 58 | male | 7 | 1 | focal onset | normal | unknown | left ankle |
| 59 | male | 14 | 7 | generalized onset | dysplasia | structural | left ankle |
| 60 | male | 2 | 0 | generalized onset | dysplasia | unknown | left ankle |
| 61 | male | 12 | 1 | focal onset | not noted | structural | right wrist |
| 62 | male | 9 | 8 | focal onset | malformation | unknown | left ankle |
| 63 | male | 0 | 0 | unclassified | infarction | structural | right ankle |
| 64 | male | 9 | 1 | focal onset | normal | unknown | right ankle |
| 65 | male | 10 | 0 | focal onset | cyst | unknown | left ankle |
| 66 | male | 5 | unknown | focal onset | malformation | structural | right ankle |
| 67 | female | 3 | 1 | generalized onset, unclassified | normal | genetic | left ankle |
| 68 | male | 11 | unknown | generalized onset | normal | unknown | left wrist |
| 69 | male | 21 | 3 | focal onset, generalized onset | volume loss, unspecified | genetic | right ankle |

In some embodiments, the patient monitoring data may be used to evaluate whether forecasting solely based on wristband data can deliver better-than-chance and clinically meaningful performance. A prerequisite for seizure risk assessment is the reliable distinction between pre- and interictal periods. For this purpose, continuous, non-overlapping 30-second segments of wristband recordings composed of six sensor data streams (electrodermal activity (EDA), accelerometer data in three dimensions, blood volume pulse (BVP), and temperature (TEMP); see, FIG. 4, for example) were analyzed. To train the seizure forecasting neural network 224, data for each of patient 1 330, patient 2 340 through patient N−1 350 and patient N 360 were label with preictal 304 and interictal periods 303. To define preictal periods 304 during training of the algorithm, lead seizures were focused on. A lead seizure may include a clinical seizure that occurs at least two hours after a preceding seizure. A 30-second data segment is labelled as preictal 304 if it occurred between 61 minutes and one minute prior to such a seizure, thus leaving a one-minute buffer prior to seizure onset (see, FIG. 5, with the red bars indicating preictal periods 304). This preictal window definition was chosen to be commensurate with other seizure forecasting research using EEG and ECoG and to account for potential small ambiguities in determining the exact seizure onset between EEG and wristband. 30-second data segments were classified as interictal 303, if they were two hours or more away from any seizure (see, FIG. 5, with interictal periods 303 indicated in green). Electrographic seizure onset was determined using video and EEG recordings. All epileptic seizure types occurring in a patient were analyzed, which included focal and primary and secondary generalized seizures (see, Table 1), as determined by board-certified epileptologists. To allow stable recording conditions, data from the first and last hour of each recording was removed from further analysis.

Preparation of Training, Validation and Test Data

For the main results, a leave-one-out cross-validation approach was applied where data from 68 patients were used for training (training set 301), and testing was done on the full dataset of the one remaining out-of-sample patient (testing set 302). This allows for maximization of the number of patients included in training and testing. Additional analyses were performed to train on lower number of patients and use other patients for validation before testing on one out-of-sample test patient (see, FIG. 7 and FIG. 10).

Figure 6:
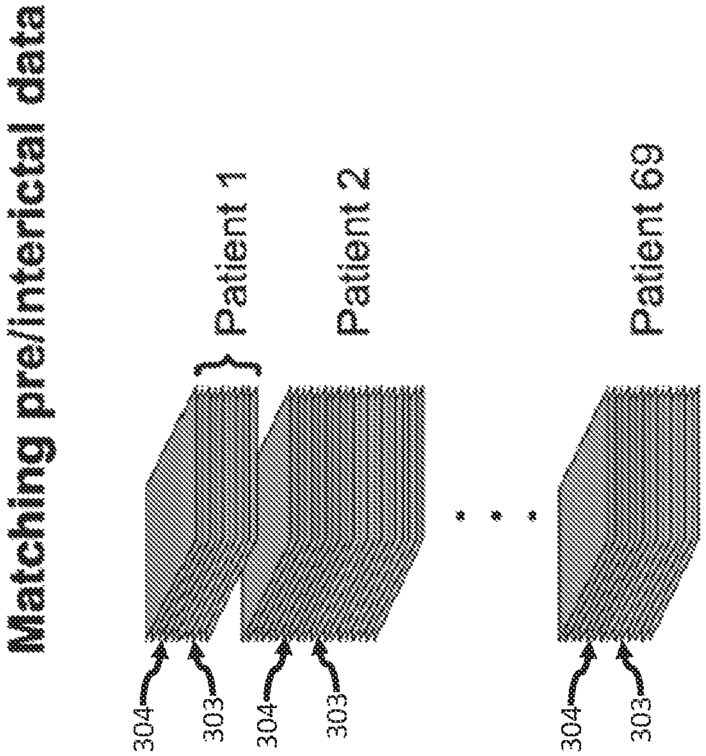
FIG. 6 depicts an outline of data processing for seizure forecasting including, for each patient, preictal segments matched with the same number of interictal segments in accordance with one or more embodiments of the present invention.

For the preparation of the training datasets 301, all 30-second preictal segments (preictal 331, preictal 341 through preictal 351) were identified and matched with an equal number of randomly chosen interictal segments in each patient (interictal 332, interictal 342 through interictal 352, see FIG. 6). This matching facilitates handling the imbalanced data during training (interictal data mostly outnumber preictal data by a large factor in each patient). Next, the matched data from 68 patients are used for training while testing was generally performed on the remaining patient's 360 full dataset.

Analysis may also be performed on training data with less than 68 patients where the remaining patients (apart from the test patient) are used for validation. Based on monitoring these validation data, a prevention of overfitting may be validated (see, FIG. 7; in this case: training on 67 patients, validation on 1 patient). Thus, the seizure forecasting neural network 224 may be trained with a 68 patient training dataset 301, and tested with a one patient testing dataset 302.

Neural Networks and Training

In some embodiments, the seizure forecasting neural network 224 employs long short-term memory networks (LSTMs), as they are specifically designed for learning underlying representations in timeseries data and have been shown to provide robust classification performance based on multi-dimensional timeseries data. To use the wristband sensor data in a LSTM networks, data was down-sampled (e.g., using the sampler 222 described above) to 4 Hz for all sensors in order to provide the same vector length for each 30-second segment (i.e. 120 sampling points). To limit LSTMs from overfitting, network architecture may kept simple and shallow (Table 1, FIG. 7), and training may be performed on matched data, i.e. where both classes appeared equally often. As stated above, no indication of significant overfitting was observed in learning metrics upon testing (see, FIG. 7).

In some embodiments, the training may be performed by using the LSTMs of the seizure forecasting neural network 224 to predict a binary classification of preictal periods, and comparing the classification to the labeled data of the training dataset 301 with an optimizer 326 to determine a loss. In some embodiments, the optimizer 326 may employ an optimization function such as, e.g., gradient descent with backpropagation through time, connectionist temporal classification (CTC), neural evolution, or other optimization technique. Thus, the optimizer 326 may determine an error between the predictions of the seizure forecasting neural network 224 and adjust LSTM parameters to improve accuracy. In some embodiments, the seizure forecasting neural network 224 was trained for 200 epochs (see, FIG. 8). Analyses may be performed using, e.g., Python and Keras with Tensorflow backend.

Performance Metrics and Statistical Tests

Figure 12:
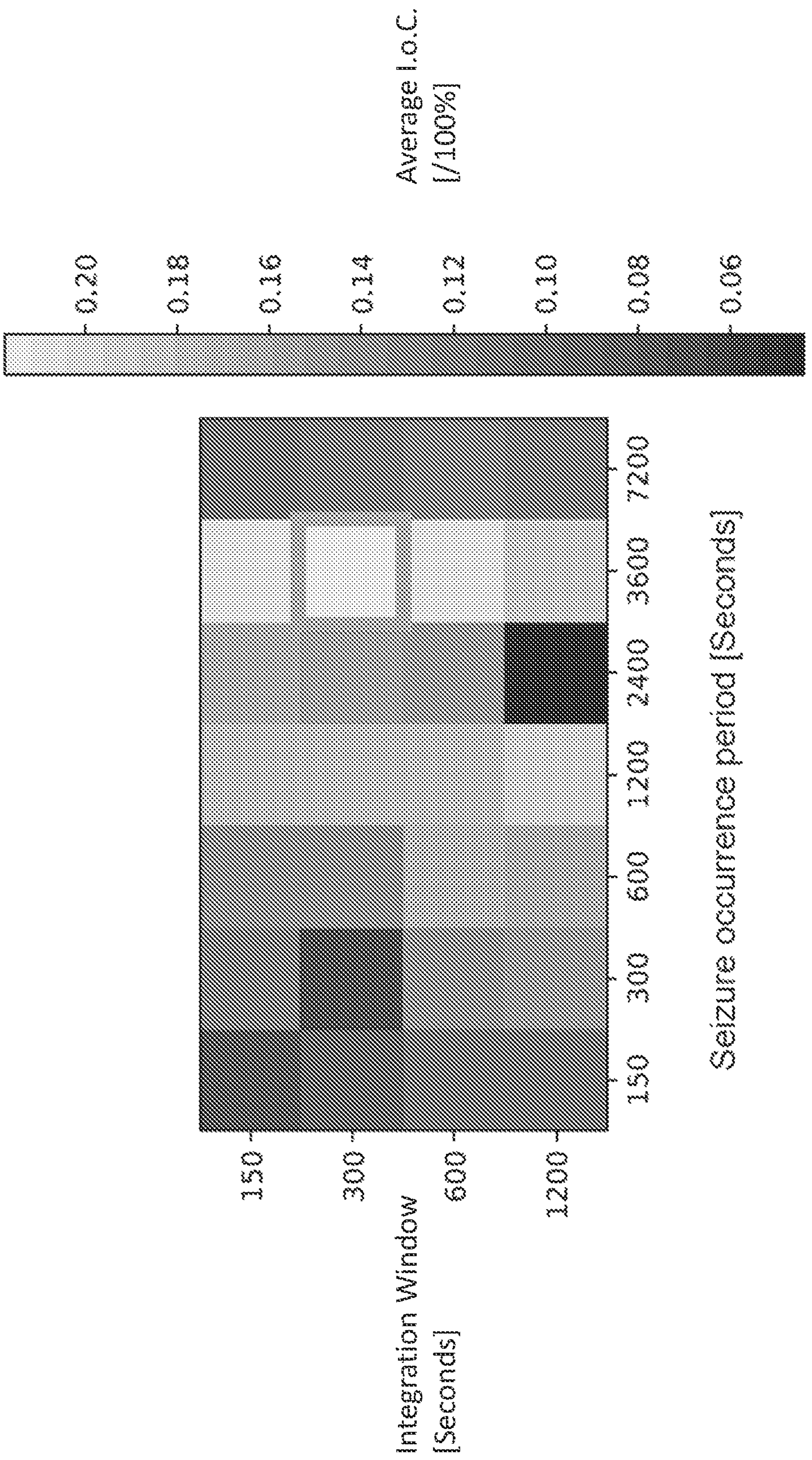
FIG. 12 depicts a grid search for finding optimal parameters determined from all patients except the patient in testing where the average IoC was obtained across 68 patients (leaving the one test patient out) for a range of values (integration window, seizure occurrence period, thresholds) with the plot showing an example for one test patient in accordance with one or more embodiments of the present invention.
Figure 13:
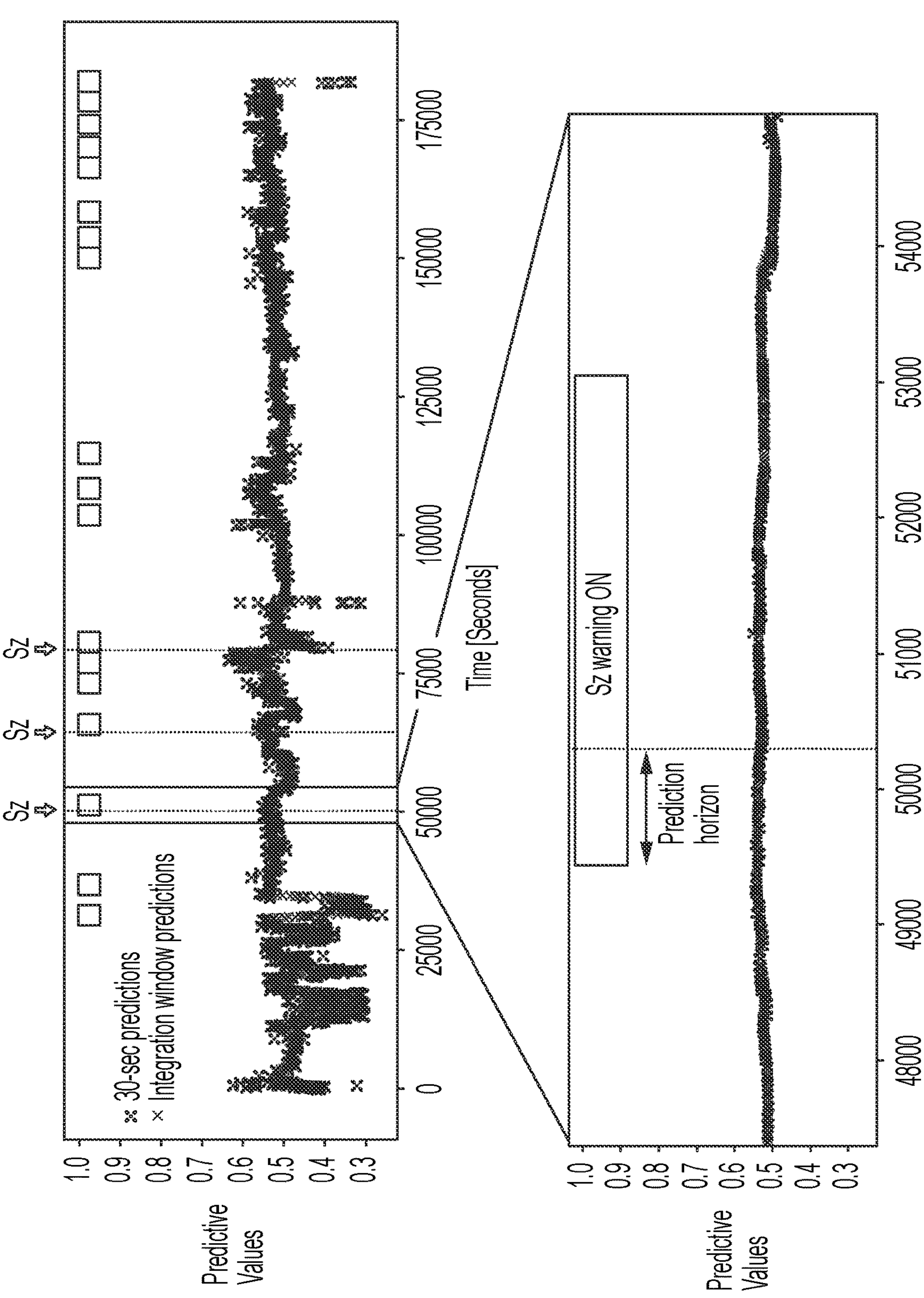
FIG. 13 depicts an illustration of the forecasting method in one patient where seizure onsets are marked by vertical lines (Sz), predictions from 30-second segments (crosses) are averaged in integration windows (here: 300 seconds duration; fill shading) with an alarm initiated once this averaged signal crosses a threshold (here: 0.54) and remains active for the duration of the seizure occurrence period (here: 3600 seconds; red shaded areas) in accordance with one or more embodiments of the present invention.

Seizure forecasting performance may be assessed on the full timeseries data (after removal of potential dropouts, e.g. when the wristband was replaced by a new one for charging purposes) from out-of-sample test patients. FIG. 13 shows the full data from one exemplary test patient. To be clinically useful, the binary classification may be translated into a suitable user interface. In some embodiments, a sliding window approach is used in which the individual 30-second segment predictions are averaged over an integration window. If this averaged value crossed a threshold, an alarm would be initiated which would last for the duration of a seizure occurrence period. A new alarm could only be initiated once the seizure occurrence period had passed (FIG. 13). This post-processing thus utilizes a determination of three additional variables: integration window, threshold and seizure occurrence period. In long-term recordings, parameters like this can in principle be optimized at the individual patient level, for example by optimizing these parameters during an initial adjustment phase. Using leave-one-out cross-validation approach, the training data is used to find the optimal parameters using a grid search implemented by a loss validation engine 328 (FIG. 12; integration window values: 150, 300, 600, 1200 seconds; seizure occurrence period values: 150, 300, 600, 1200, 2400, 3600, 7200 seconds; threshold values: 0.5, 0.52, 0.54, 0.56, 0.58, 0.6). This means that, for forecasting of a test patient N 360 using a seizure forecasting neural network 224 trained on 68 patients of the training dataset 301, the parameters yielding the on average highest IoC for predictions on the training data predictions from these 68 patients were chosen (FIG. 12, blue square). Note that this parameter selection process ensures that no information from the test patient is used to infer these three parameters. This grid search yields highly similar results across patients (since training datasets overlap by 67 patients) and provides an integration window of 600 seconds, seizure occurrence period of 3600 seconds and threshold of 0.54 as the best parameter set in all ten cases where it is applied (FIG. 12). However, other parameters also may yield good forecasting performance results. As stated above, these parameters can be further optimized for the individual patient, for example by determining these parameters during an initial training period or to tune sensitivity versus time in warning to suit the individual patient's needs.

As clinically useful metrics to evaluate forecasting algorithm performance, the loss validation engine 328 may employ metrics including: sensitivity (i.e. the true positive seizure prediction rate; seizures outside the recording period were not considered), time in warning (i.e. the fraction of time spent in warning) and improvement over chance (IoC, defined as the difference between sensitivity and time in warning). Mean prediction scores may be determined for these variables over ten independent runs for each patient where each run corresponds to an independently trained seizure forecasting neural network 224.

A two-sided Wilcoxon signed-rank test may used by the loss validation engine 328 to assess significance of IoC-values in each patient. Multiple comparisons may be controlled for using a Benjamini and Hochberg false discovery rate using a threshold of 0.05.29 A two-sided Mann-Whitney U test may be applied for comparison between groups. In some embodiments, a p of 0.05 or less may be significant.

Results

Figure 7:
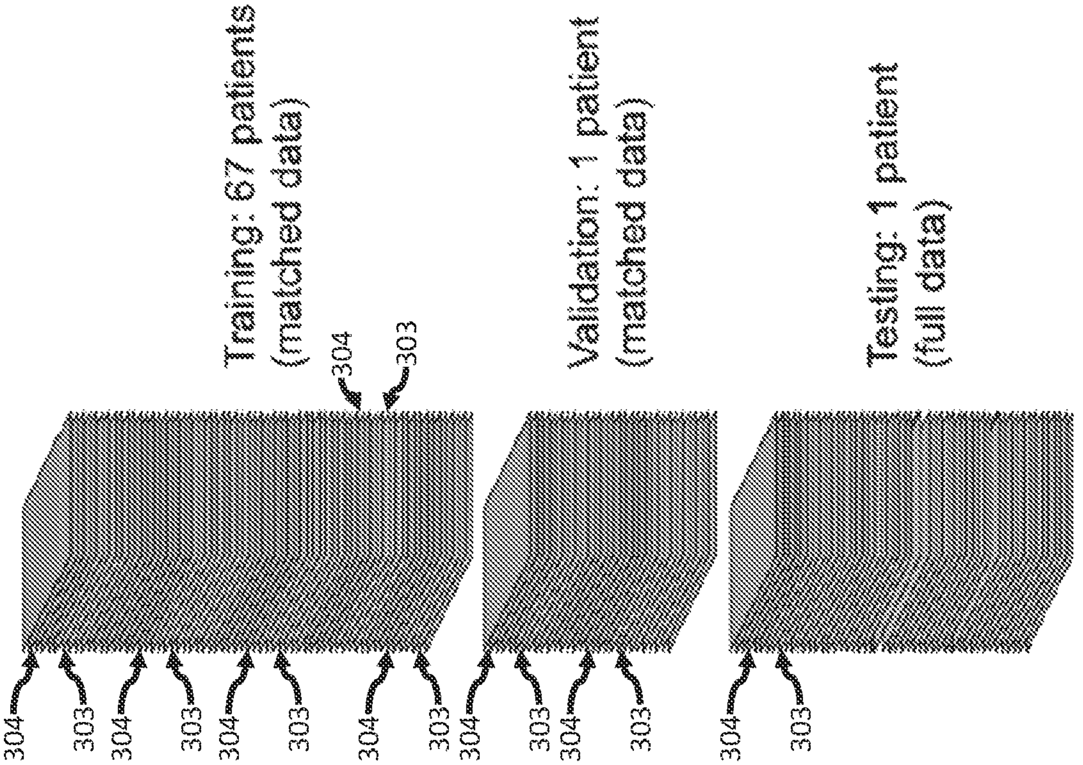
FIG. 7 depicts an outline of data processing for seizure forecasting including a schematic outline of separation into training, validation and test data in accordance with one or more embodiments of the present invention.
Figure 8:
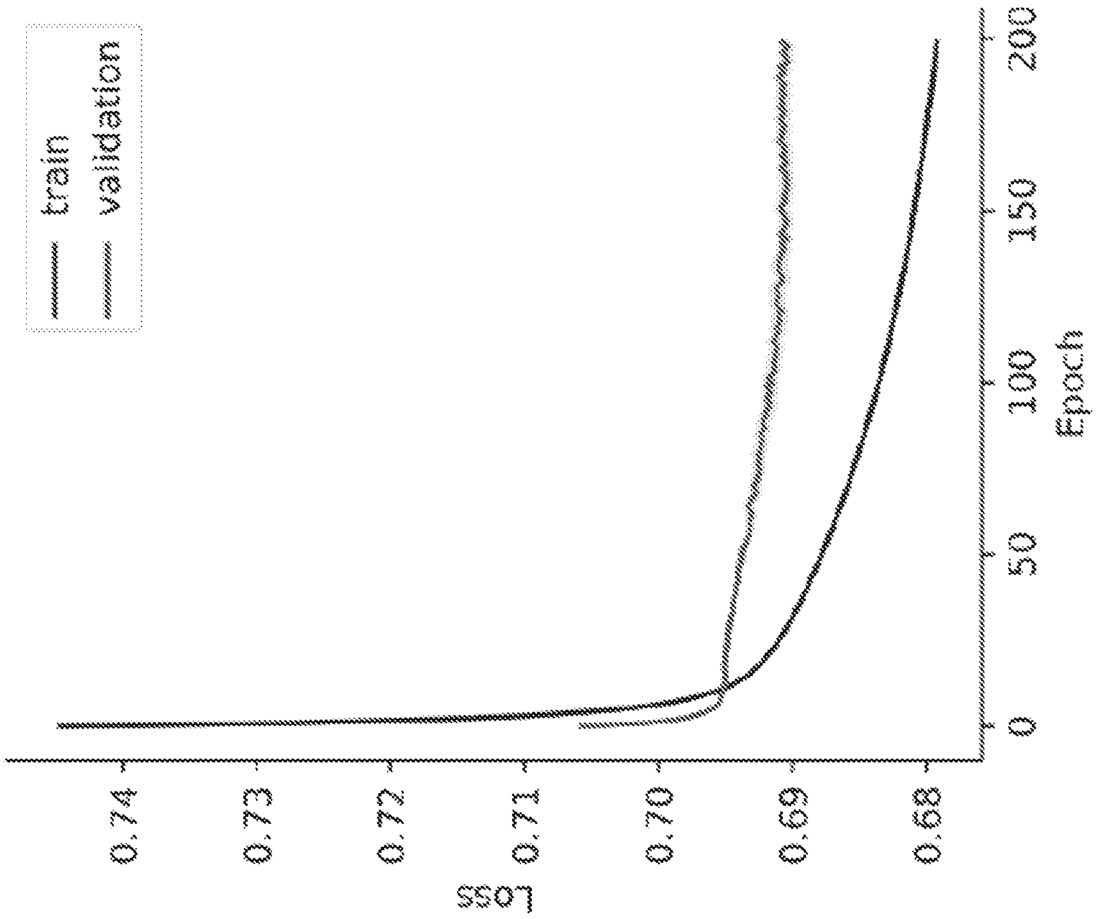
FIG. 8 depicts an outline of data processing for seizure forecasting including a training (67 patients) and validation (1 patient) loss where the solid line and errors indicate mean plus or minus standard error of the mean (s.e.m.) across all patients in accordance with one or more embodiments of the present invention.
Figure 9:
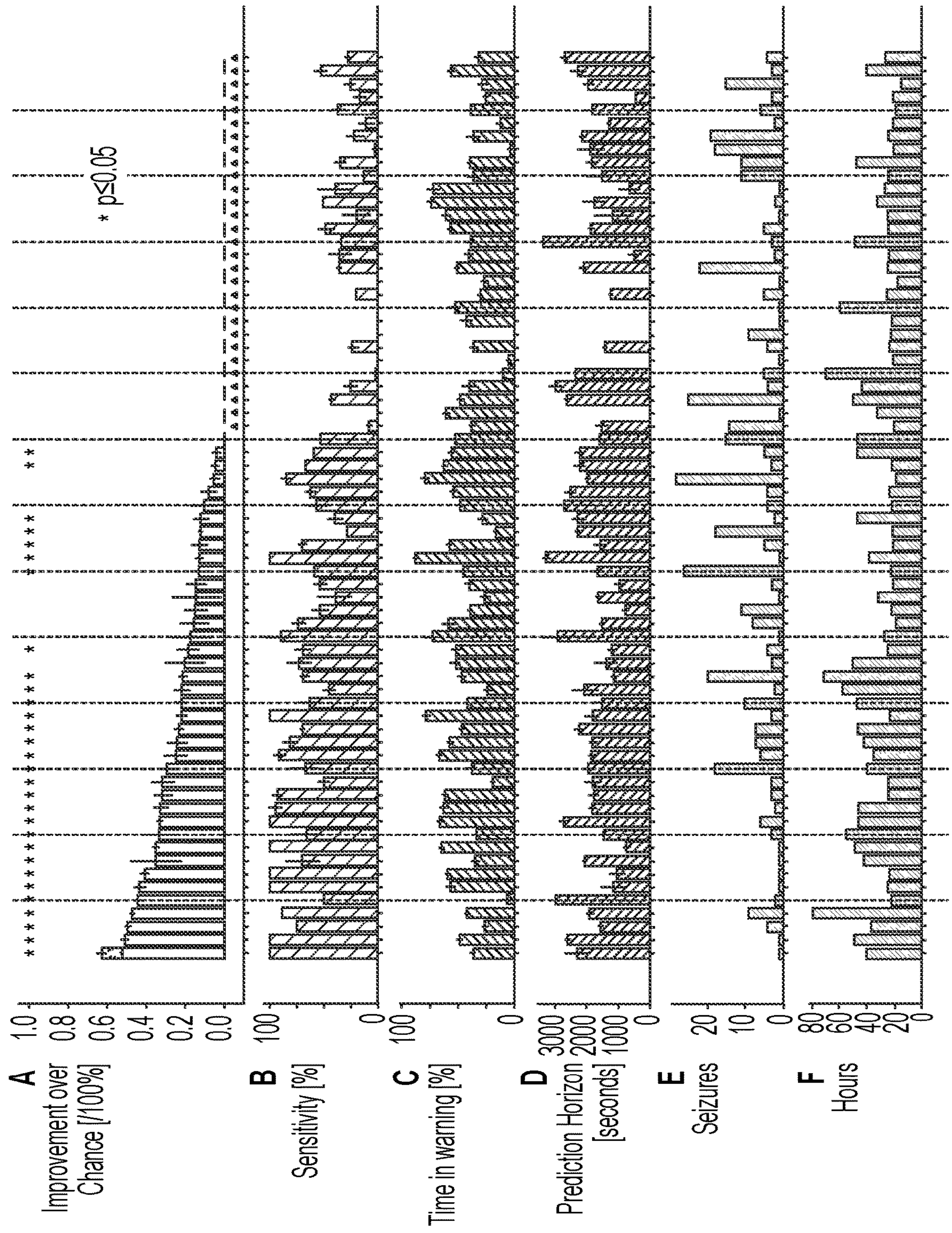
FIG. 9 depicts forecasting performance results in a pseudo-prospective approach for all patients. Bars represent mean values over ten runs, error bars indicate s.e.m. A, improvement over chance. B, sensitivity. C, time in warning. D, prediction horizon. E, number of seizures. F, number of hours in recording in accordance with one or more embodiments of the present invention.

In some embodiments, the dataset 301 and 302 includes multi-day recordings from 69 epilepsy patients (mean age 9.8±5.9 years (mean±s.d.), 28 female, total duration 2311.4 hours, 452 seizures; Table 3). The performance of the proposed seizure forecasting system is evaluated in terms of sensitivity, time in warning and improvement over chance (IoC). A leave-one-out cross-validation approach is applied where matched pre-/interictal data from 68 patients are used for training (FIG. 6), and testing was done on the full dataset of the one remaining out-of-sample patient. Control analyses indicates no signs of significant overfitting during training (FIG. 7). Performance may be calculated for predictions from ten independently trained long short-term memory (LSTM, Table 1) networks for each patient. FIG. 9 shows the average performance for all 69 patients. Significant IoC is an indication that seizure forecasting is useful in a clinical setting. In this data, seizure forecasting was significantly better than chance for 43.5% of patients (30 out of 69 patients). For these patients, a mean IoC of 28.5±2.6%, a mean sensitivity of 75.6±3.8% and a mean time in warning of 47.2±3.4% (mean±s.e.m) was obtained. Across all patients, including the ones with non-significant, non-positive IoC, mean IoC was 14.1±1.9%, mean sensitivity was 51.2±3.8% and mean time in warning was 43.7±2.3%. Note that mean IoC in patients with non-positive mean IoC was set to zero prior to averaging across patients.

For practical application as a warning system for patients the expected time between alarm onset and seizure onset, the prediction horizon (FIG. 13), is of particular interest. A sufficiently long alarm may afford patients to take precautionary steps or avoid certain activities. The mean prediction horizon across all patients observed was 1844±80 seconds, a period that may afford reasonable warning in advance.

Prediction performance being dependent on seizure type may also be assessed, in particular whether performance depends on seizures of focal or generalized onset. Thus, prediction performance between patients was compared with only focal onset seizures (n=35 patients) and patients with only generalized onset of seizures (n=16 patients; Table 3). Group comparison reveals no significant difference in IoC values (p=0.44). Similarly, no significant dependence on where the device was worn (wrist: n=31 patients, ankle: n=38 patients) in terms of IoC performance values was revealed by group comparison (p=0.24).

Figure 10:
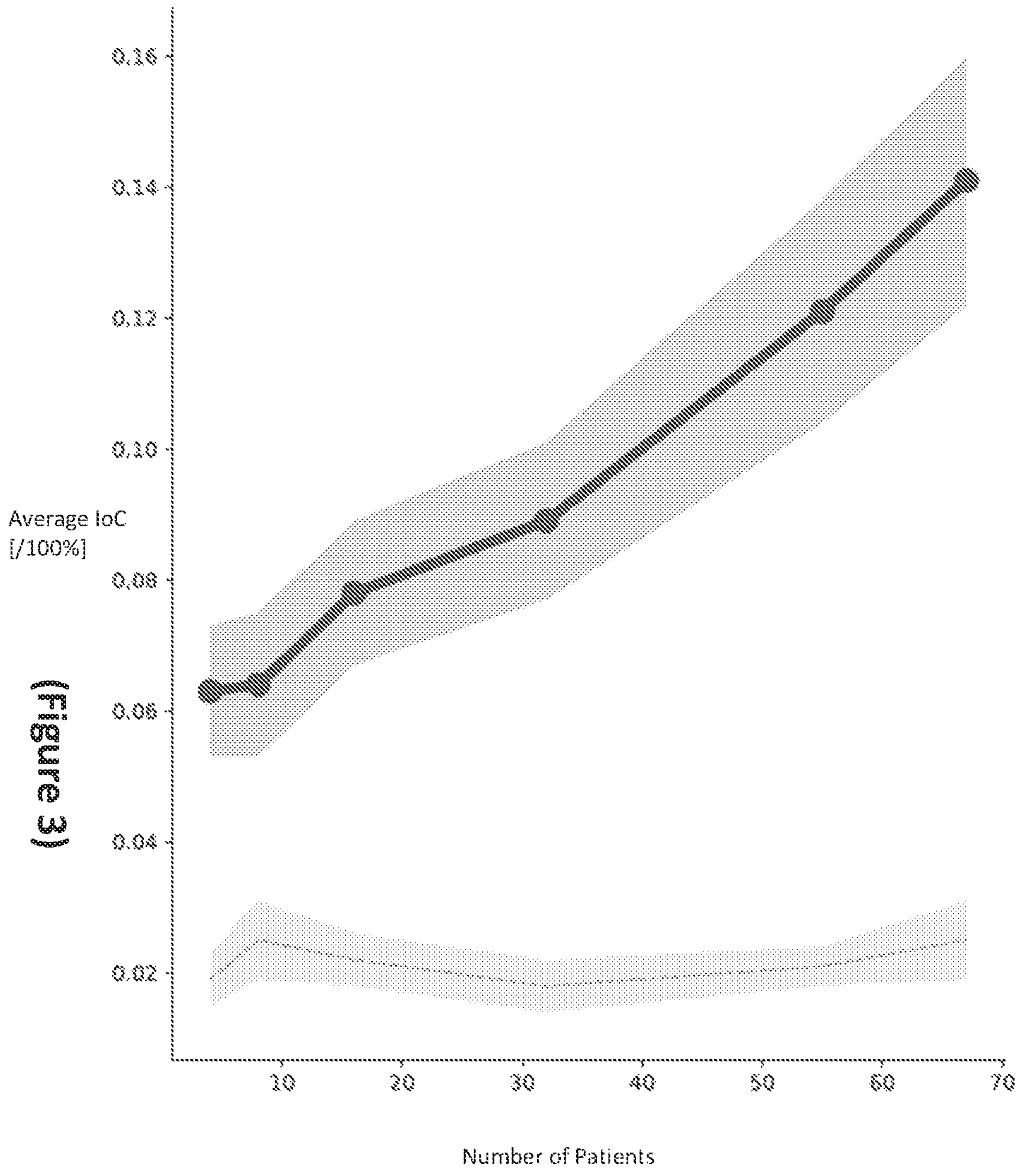
FIG. 10 depicts seizure forecasting performance improves with larger training datasets where blue indicates the average improvement over chance for increasing sizes of training data when performance is assessed at the individual patient level (test data) where training of neural network was performed with training data comprised of 4, 8, 16, 32, 55 or 68 patients with the plot indicating averages across all patients (mean±s.e.m.), and where the gray depicts average improvement over chance for time-shuffled predictions in accordance with one or more embodiments of the present invention.

Machine leaning, and particularly deep learning, benefits from large datasets that afford learning of the underlying data representations while also containing enough variability to permit generalization to unseen data. In such a use-case, performance may take a certain amount of data and, more generally, benefits from training on larger datasets. To determine the relationship between seizure forecasting performance and size of the training dataset, and to obtain a better understanding of how a deep learning approach might benefit from more data in the future, performance may be evaluated under different amounts of training data. For this purpose, instead of training on all 68 patients in a leave-one-out approach, as described above, the amount of training data may be systematically reduced by considering only a smaller number of patients (n=4, 8, 16, 32 or 55 patients) for training. Specifically, performance for each test patient was calculated for ten independently trained networks where training data was composed of only n number of randomly chosen patients in each run. FIG. 10 shows the dependence of forecasting performance in term of average IoC across all patients (mean IoC in patients with non-positive mean IoC again set to zero prior to averaging). Performance increased monotonically as more patients were used for training. These results demonstrate the benefits of creating larger dataset for training. As no saturation effect under larger training size is apparent these results suggest that larger datasets than, on average, may improve seizure forecasting performance even more. Accordingly, training datasets exceed 100 patients, 200 patients or more are contemplated.

Example 2—Training a 1DConv-Based Seizure Forecasting Model

In some embodiments, the patients 301 and 302 were also used to train and test a seizure forecasting neural network 224 using the leave one out cross validation approach described above for the LSTM-based seizure forecasting model. For the 1DConv-based seizure forecasting neural network 224, preprocessing and the preparation of the training dataset 301, validation and testing dataset 302 are the same. However, for the 1DConv-based seizure forecasting neural network 224, the seizure forecasting neural network 224 employs a 1-dimensional convolutional neural network. 1DConv networks may be easier and faster to train than LSTM networks while also exhibiting good performance on timeseries data. Table 2 shows a summary of the 1DConv network parameters used. Similar to the LSTM network, the 1DConv network was trained for 200 epochs with analyses performed with in- house written code using, e.g., Python and Keras with Tensorflow backend.

Similar to the LSTM networks described above, data was down-sampled (e.g., using the sampler 222 described above) to 4 Hz for all sensors in order to provide the same vector length for each 30-second segment (i.e. 120 sampling points) for input to the 1DConv networks. To limit 1DConv networks from overfitting, network architecture may kept simple and shallow (Table 2), and training may be performed on matched data, i.e. where both classes appeared equally often.

In some embodiments, the training may be performed by using the 1DConv-based seizure forecasting neural network 224 to predict a binary classification of preictal periods, and comparing the classification to the labeled data of the training dataset 301 with an optimizer 326 to determine a loss. In some embodiments, the optimizer 326 may employ an optimization function such as, e.g., gradient descent with backpropagation through time, connectionist temporal classification (CTC), neural evolution, or other optimization technique. Thus, the optimizer 326 may determine an error between the predictions of the seizure forecasting neural network 224 and adjust 1DConv parameters to improve accuracy. In some embodiments, the seizure forecasting neural network 224 was trained for 200 epochs.

Performance Metrics and Statistical Tests

Seizure forecasting performance may be assessed on the full timeseries data (after removal of potential dropouts, e.g. when the wristband was replaced by a new one for charging purposes) from out-of-sample test patients. FIG. 13 shows the full data from one exemplary test patient. To be clinically useful, the binary classification may be translated into a suitable user interface. In some embodiments, the sliding window approach described above with reference to Example 1 is used in which the individual 30-second segment predictions are averaged over an integration window, and if this averaged value crossed a threshold, an alarm would be initiated which would last for the duration of a seizure occurrence period. A new alarm could only be initiated once the seizure occurrence period had passed.

Using leave-one-out cross-validation approach, the training data is used to find the optimal parameters using a grid search implemented by the loss validation engine 328 (FIG. 12; integration window values: 150, 300, 600, 1200 seconds; seizure occurrence period values: 150, 300, 600, 1200, 2400, 3600, 7200 seconds; threshold values: 0.5, 0.52, 0.54, 0.56, 0.58, 0.6).

As clinically useful metrics to evaluate forecasting algorithm performance, the loss validation engine 328 may employ metrics including: sensitivity (i.e. the true positive seizure prediction rate; seizures outside the recording period were not considered), time in warning (i.e. the fraction of time spent in warning) and improvement over chance (IoC, defined as the difference between sensitivity and time in warning). Mean prediction scores may be determined for these variables over ten independent runs for each patient where each run corresponds to an independently trained seizure forecasting neural network 224.

A two-sided Wilcoxon signed-rank test may used by the loss validation engine 328 to assess significance of IoC-values in each patient. Multiple comparisons may be controlled for using a Benjamini and Hochberg false discovery rate using a threshold of 0.05.29 A two-sided Mann-Whitney U test may be applied for comparison between groups. In some embodiments, a p of 0.05 or less may be significant.

Results

In some embodiments, the dataset 301 and 302 includes multi-day recordings from 69 epilepsy patients (mean age 9.8±5.9 years (mean±s.d.), 28 female, total duration 2311.4 hours, 452 seizures; Table 3). The performance of the proposed seizure forecasting system is evaluated in terms of sensitivity, time in warning and improvement over chance (IoC). A leave-one-out cross-validation approach is applied where matched pre-/interictal data from 68 patients are used for training (FIG. 6), and testing was done on the full dataset of the one remaining out-of-sample patient. Control analyses indicates no signs of significant overfitting during training (FIG. 7). Performance may be calculated for predictions from ten independently trained 1DConv network (1DConv, Table 2) networks for each patient. Significant IoC is an indication that seizure forecasting is useful in a clinical setting. In this data, seizure forecasting was significantly better than chance for 43.5% of patients (30 out of 69 patients).

Prediction performance between patients was compared with only focal onset seizures (n=35 patients) and patients with only generalized onset of seizures (n=16 patients; Table 3). Group comparison reveals no significant difference in IoC values (p=0.44). Similarly, no significant dependence on where the device was worn (wrist: n=31 patients, ankle: n=38 patients) in terms of IoC performance values was revealed by group comparison (p=0.24).

Figure 11:
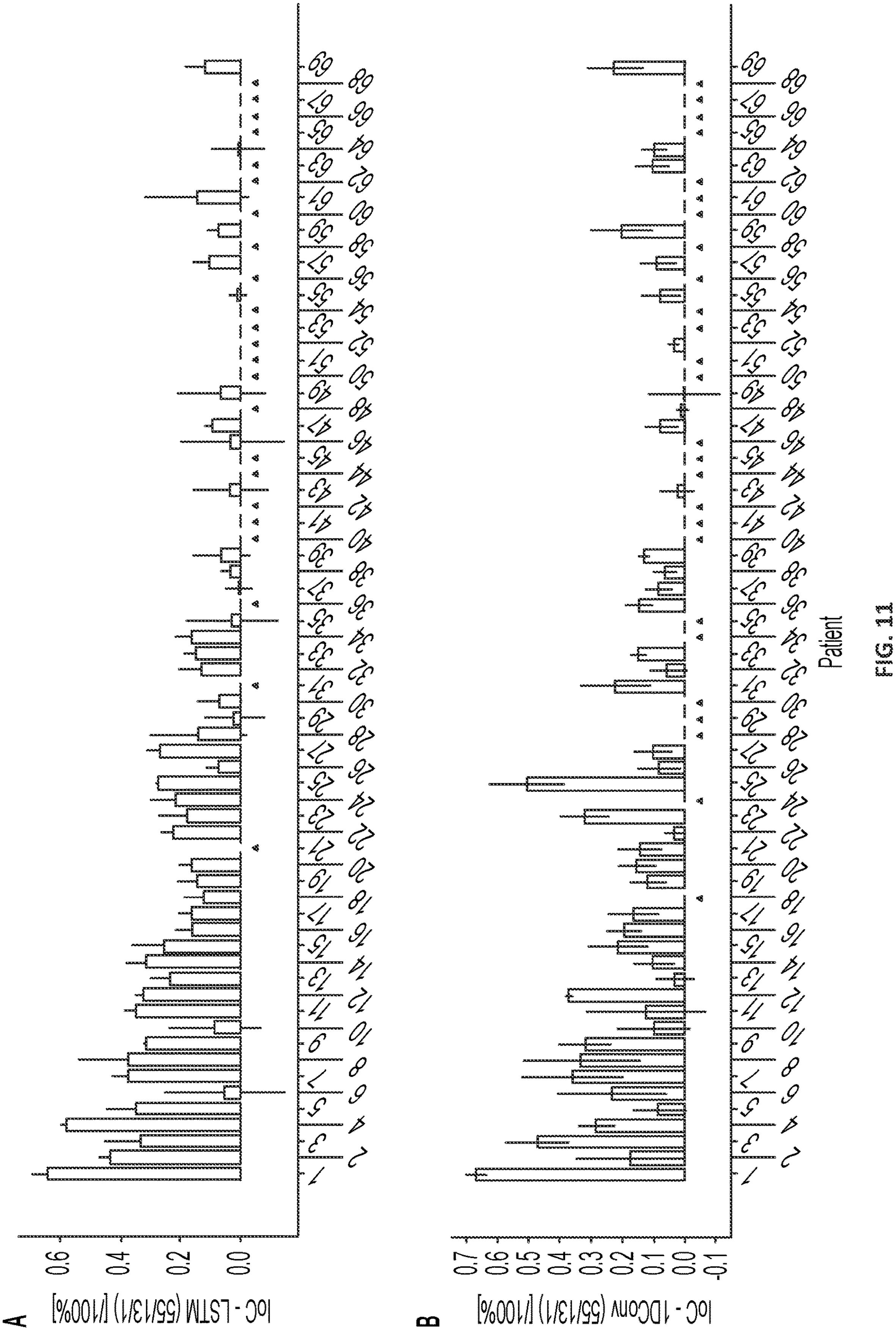
FIG. 11 depicts an LSTM network approach A (average IoC 12.2±1.78%) that performed on average better than a method based on a 1-dimensional convolutional network B (average IoC 10.8±1.70%; mean±s.e.m., five independent runs) in accordance with one or more embodiments of the present invention.

FIG. 11 shows a comparison in performance between the LSTM-based seizure forecasting model described above and the 1DConv-based seizure forecasting model. As shown, the average IoC for 1DConv had a mean±s.e.m. of 10.8±1.70%, as compared to 12.2±1.78% for the LSTM-based model. Accordingly, the LSTM-based performed, on average, better than 1DConv.

Figure 14:
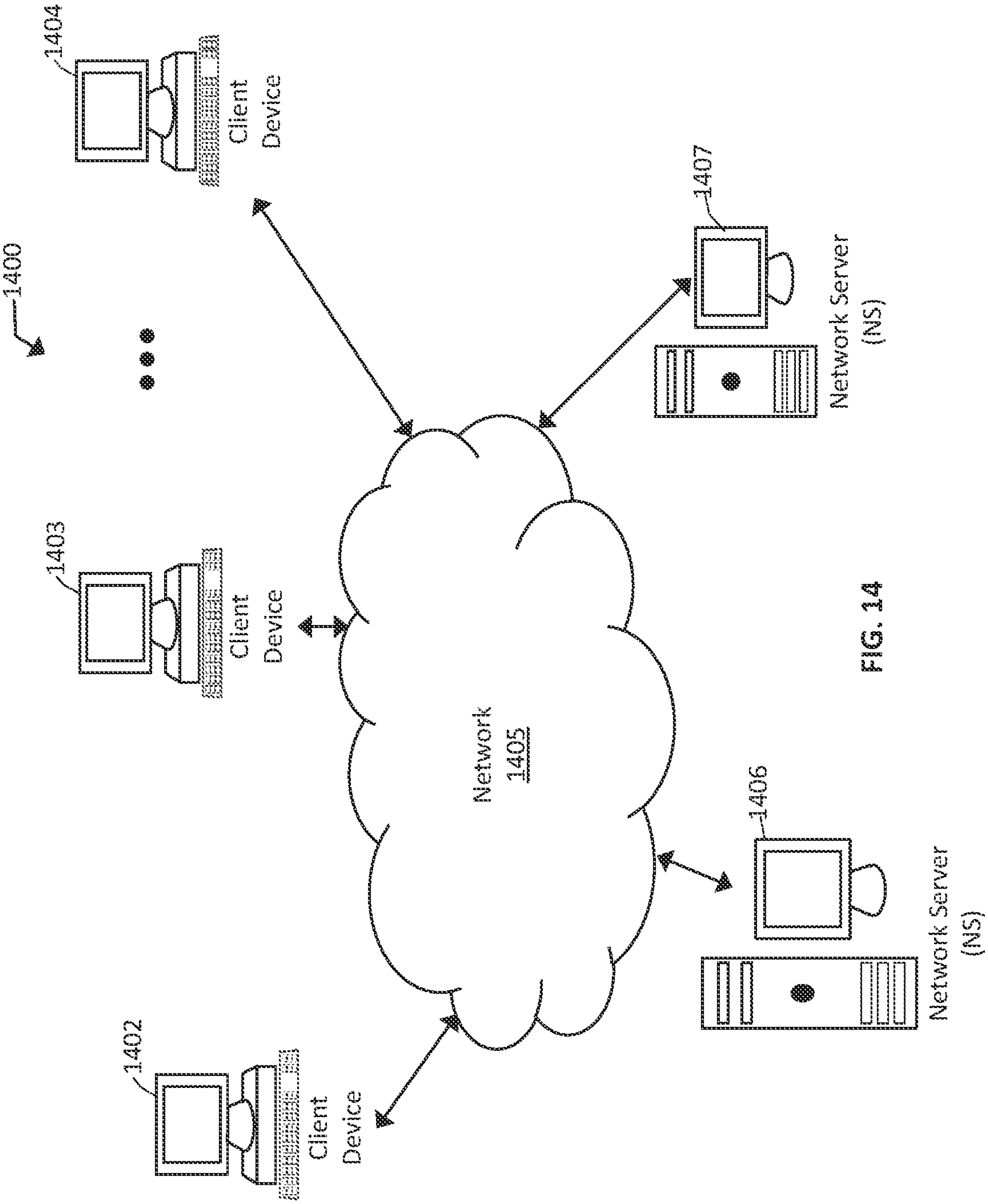
FIG. 14 depicts a block diagram of an exemplary computer-based system and platform 1400 in accordance with one or more embodiments of the present disclosure.

FIG. 14 depicts a block diagram of an exemplary computer-based system and platform 1400 in accordance with one or more embodiments of the present disclosure. However, not all of these components may be required to practice one or more embodiments, and variations in the arrangement and type of the components may be made without departing from the spirit or scope of various embodiments of the present disclosure. In some embodiments, the illustrative computing devices and the illustrative computing components of the exemplary computer-based system and platform 1400 may be configured to manage a large number of members and concurrent transactions, as detailed herein. In some embodiments, the exemplary computer-based system and platform 1400 may be based on a scalable computer and network architecture that incorporates varies strategies for assessing the data, caching, searching, and/or database connection pooling. An example of the scalable architecture is an architecture that is capable of operating multiple servers.

In some embodiments, referring to FIG. 14, members 1402-1404 (e.g., clients) of the exemplary computer-based system and platform 1400 may include virtually any computing device capable of receiving and sending a message over a network (e.g., cloud network), such as network 1405, to and from another computing device, such as servers 1406 and 1407, each other, and the like. In some embodiments, the member devices 1402-1404 may be personal computers, multiprocessor systems, microprocessor-based or programmable consumer electronics, network PCs, and the like. In some embodiments, one or more member devices within member devices 1402-1404 may include computing devices that typically connect using a wireless communications medium such as cell phones, smart phones, pagers, walkie talkies, radio frequency (RF) devices, infrared (IR) devices, CBs, integrated devices combining one or more of the preceding devices, or virtually any mobile computing device, and the like. In some embodiments, one or more member devices within member devices 1402-1404 may be devices that are capable of connecting using a wired or wireless communication medium such as a PDA, POCKET PC, wearable computer, a laptop, tablet, desktop computer, a netbook, a video game device, a pager, a smart phone, an ultra-mobile personal computer (UMPC), and/or any other device that is equipped to communicate over a wired and/or wireless communication medium (e.g., NFC, RFID, NBIOT, 3G, 4G, 5G, GSM, GPRS, WiFi, WiMax, CDMA, satellite, ZigBee, etc.). In some embodiments, one or more member devices within member devices 1402-1404 may include may run one or more applications, such as Internet browsers, mobile applications, voice calls, video games, videoconferencing, and email, among others. In some embodiments, one or more member devices within member devices 1402-1404 may be configured to receive and to send web pages, and the like. In some embodiments, an exemplary specifically programmed browser application of the present disclosure may be configured to receive and display graphics, text, multimedia, and the like, employing virtually any web based language, including, but not limited to Standard Generalized Markup Language (SMGL), such as HyperText Markup Language (HTML), a wireless application protocol (WAP), a Handheld Device Markup Language (HDML), such as Wireless Markup Language (WML), WMLScript, XML, JavaScript, and the like. In some embodiments, a member device within member devices 1402-1404 may be specifically programmed by either Java, .Net, QT, C, C++ and/or other suitable programming language. In some embodiments, one or more member devices within member devices 1402-1404 may be specifically programmed include or execute an application to perform a variety of possible tasks, such as, without limitation, messaging functionality, browsing, searching, playing, streaming or displaying various forms of content, including locally stored or uploaded messages, images and/or video, and/or games.

In some embodiments, the exemplary network 1405 may provide network access, data transport and/or other services to any computing device coupled to it. In some embodiments, the exemplary network 1405 may include and implement at least one specialized network architecture that may be based at least in part on one or more standards set by, for example, without limitation, Global System for Mobile communication (GSM) Association, the Internet Engineering Task Force (IETF), and the Worldwide Interoperability for Microwave Access (WiMAX) forum. In some embodiments, the exemplary network 1405 may implement one or more of a GSM architecture, a General Packet Radio Service (GPRS) architecture, a Universal Mobile Telecommunications System (UMTS) architecture, and an evolution of UMTS referred to as Long Term Evolution (LTE). In some embodiments, the exemplary network 1405 may include and implement, as an alternative or in conjunction with one or more of the above, a WiMAX architecture defined by the WiMAX forum. In some embodiments and, optionally, in combination of any embodiment described above or below, the exemplary network 1405 may also include, for instance, at least one of a local area network (LAN), a wide area network (WAN), the Internet, a virtual LAN (VLAN), an enterprise LAN, a layer 3 virtual private network (VPN), an enterprise IP network, or any combination thereof. In some embodiments and, optionally, in combination of any embodiment described above or below, at least one computer network communication over the exemplary network 1405 may be transmitted based at least in part on one of more communication modes such as but not limited to: NFC, RFID, Narrow Band Internet of Things (NBIOT), ZigBee, 3G, 4G, 5G, GSM, GPRS, WiFi, WiMax, CDMA, satellite and any combination thereof. In some embodiments, the exemplary network 1405 may also include mass storage, such as network attached storage (NAS), a storage area network (SAN), a content delivery network (CDN) or other forms of computer or machine readable media.

In some embodiments, the exemplary server 1406 or the exemplary server 1407 may be a web server (or a series of servers) running a network operating system, examples of which may include but are not limited to Microsoft Windows Server, Novell NetWare, or Linux. In some embodiments, the exemplary server 1406 or the exemplary server 1407 may be used for and/or provide cloud and/or network computing. Although not shown in FIG. 14, in some embodiments, the exemplary server 1406 or the exemplary server 1407 may have connections to external systems like email, SMS messaging, text messaging, ad content providers, etc. Any of the features of the exemplary server 1406 may be also implemented in the exemplary server 1407 and vice versa.

In some embodiments, one or more of the exemplary servers 1406 and 1407 may be specifically programmed to perform, in non-limiting example, as authentication servers, search servers, email servers, social networking services servers, SMS servers, IM servers, MMS servers, exchange servers, photo-sharing services servers, advertisement providing servers, financial/banking-related services servers, travel services servers, or any similarly suitable service-base servers for users of the member computing devices 1401-1404.

In some embodiments and, optionally, in combination of any embodiment described above or below, for example, one or more exemplary computing member devices 1402-1404, the exemplary server 1406, and/or the exemplary server 1407 may include a specifically programmed software module that may be configured to send, process, and receive information using a scripting language, a remote procedure call, an email, a tweet, Short Message Service (SMS), Multimedia Message Service (MMS), instant messaging (IM), internet relay chat (IRC), mIRC, Jabber, an application programming interface, Simple Object Access Protocol (SOAP) methods, Common Object Request Broker Architecture (CORBA), HTTP (Hypertext Transfer Protocol), REST (Representational State Transfer), or any combination thereof.

Figure 15:
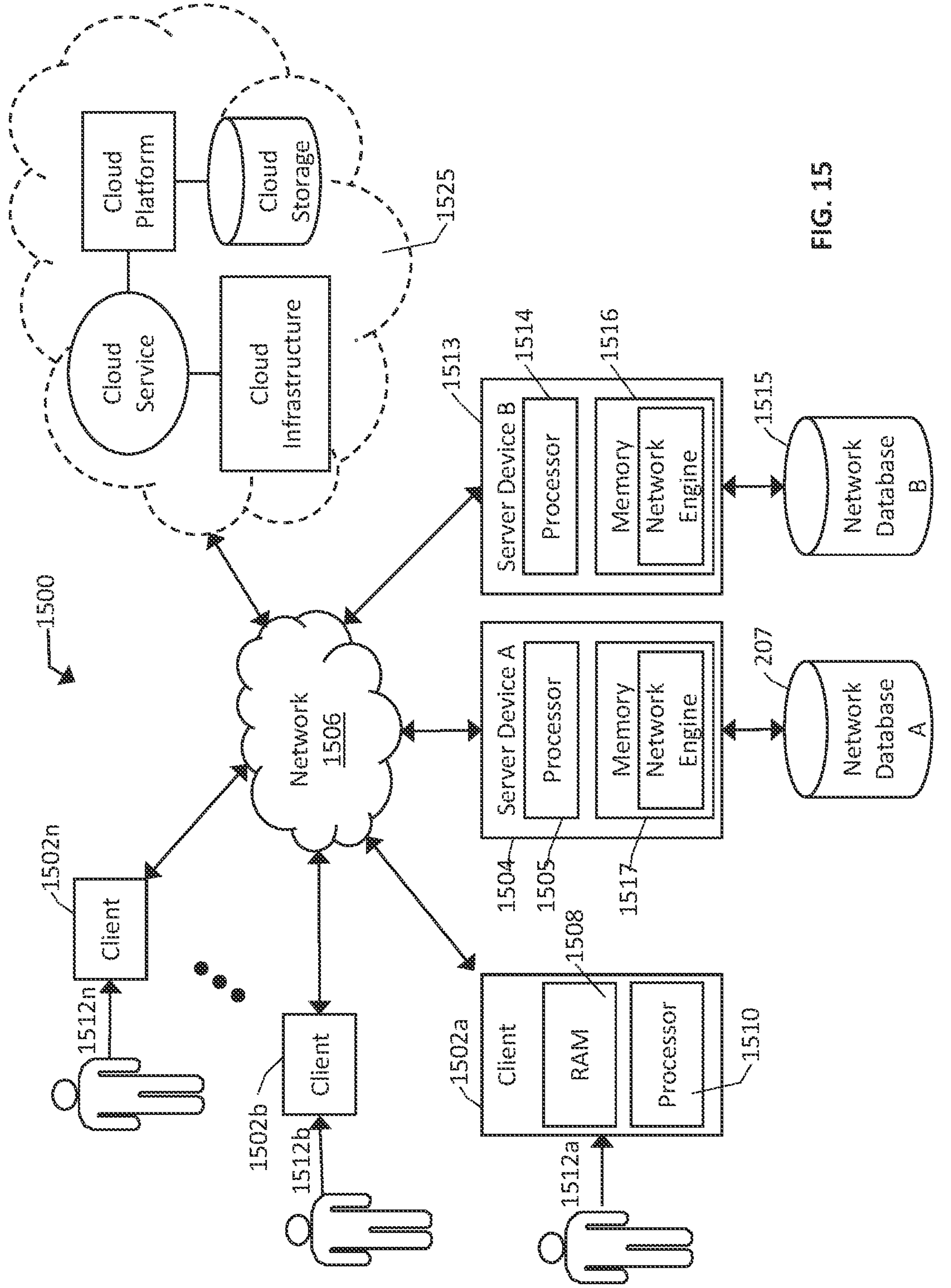
FIG. 15 depicts a block diagram of another exemplary computer-based system and platform 1500 in accordance with one or more embodiments of the present disclosure.

FIG. 15 depicts a block diagram of another exemplary computer-based system and platform 1500 in accordance with one or more embodiments of the present disclosure. However, not all of these components may be required to practice one or more embodiments, and variations in the arrangement and type of the components may be made without departing from the spirit or scope of various embodiments of the present disclosure. In some embodiments, the member computing devices 1502*a*, 1502*b* thru 1502*n* shown each at least includes a computer-readable medium, such as a random-access memory (RAM) 1508 coupled to a processor 1510 or FLASH memory. In some embodiments, the processor 1510 may execute computer-executable program instructions stored in memory 1508. In some embodiments, the processor 1510 may include a microprocessor, an ASIC, and/or a state machine. In some embodiments, the processor 1510 may include, or may be in communication with, media, for example computer-readable media, which stores instructions that, when executed by the processor 1510, may cause the processor 1510 to perform one or more steps described herein. In some embodiments, examples of computer-readable media may include, but are not limited to, an electronic, optical, magnetic, or other storage or transmission device capable of providing a processor, such as the processor 1510 of client 1502*a*, with computer-readable instructions. In some embodiments, other examples of suitable media may include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. In some embodiments, the instructions may comprise code from any computer-programming language, including, for example, C, C++, Visual Basic, Java, Python, Perl, JavaScript, and etc.

In some embodiments, member computing devices 1502*a* through 1502*n* may also comprise a number of external or internal devices such as a mouse, a CD-ROM, DVD, a physical or virtual keyboard, a display, or other input or output devices. In some embodiments, examples of member computing devices 1502*a* through 1502*n* (e.g., clients) may be any type of processor-based platforms that are connected to a network 1506 such as, without limitation, personal computers, digital assistants, personal digital assistants, smart phones, pagers, digital tablets, laptop computers, Internet appliances, and other processor-based devices. In some embodiments, member computing devices 1502*a* through 1502*n* may be specifically programmed with one or more application programs in accordance with one or more principles/methodologies detailed herein. In some embodiments, member computing devices 1502*a* through 1502*n* may operate on any operating system capable of supporting a browser or browser-enabled application, such as Microsoft™, Windows™, and/or Linux. In some embodiments, member computing devices 1502*a* through 1502*n* shown may include, for example, personal computers executing a browser application program such as Microsoft Corporation's Internet Explorer™, Apple Computer, Inc.'s Safari™, Mozilla Firefox, and/or Opera. In some embodiments, through the member computing client devices 1502*a* through 1502*n*, users, 1512*a* through 1502*n*, may communicate over the exemplary network 1506 with each other and/or with other systems and/or devices coupled to the network 1506. As shown in FIG. 15, exemplary server devices 1504 and 1513 may be also coupled to the network 1506. In some embodiments, one or more member computing devices 1502*a* through 1502*n* may be mobile clients.

In some embodiments, at least one database of exemplary databases 1507 and 1515 may be any type of database, including a database managed by a database management system (DBMS). In some embodiments, an exemplary DBMS-managed database may be specifically programmed as an engine that controls organization, storage, management, and/or retrieval of data in the respective database. In some embodiments, the exemplary DBMS-managed database may be specifically programmed to provide the ability to query, backup and replicate, enforce rules, provide security, compute, perform change and access logging, and/or automate optimization. In some embodiments, the exemplary DBMS-managed database may be chosen from Oracle database, IBM DB2, Adaptive Server Enterprise, FileMaker, Microsoft Access, Microsoft SQL Server, MySQL, PostgreSQL, and a NoSQL implementation. In some embodiments, the exemplary DBMS-managed database may be specifically programmed to define each respective schema of each database in the exemplary DBMS, according to a particular database model of the present disclosure which may include a hierarchical model, network model, relational model, object model, or some other suitable organization that may result in one or more applicable data structures that may include fields, records, files, and/or objects. In some embodiments, the exemplary DBMS-managed database may be specifically programmed to include metadata about the data that is stored.

Figure 16:
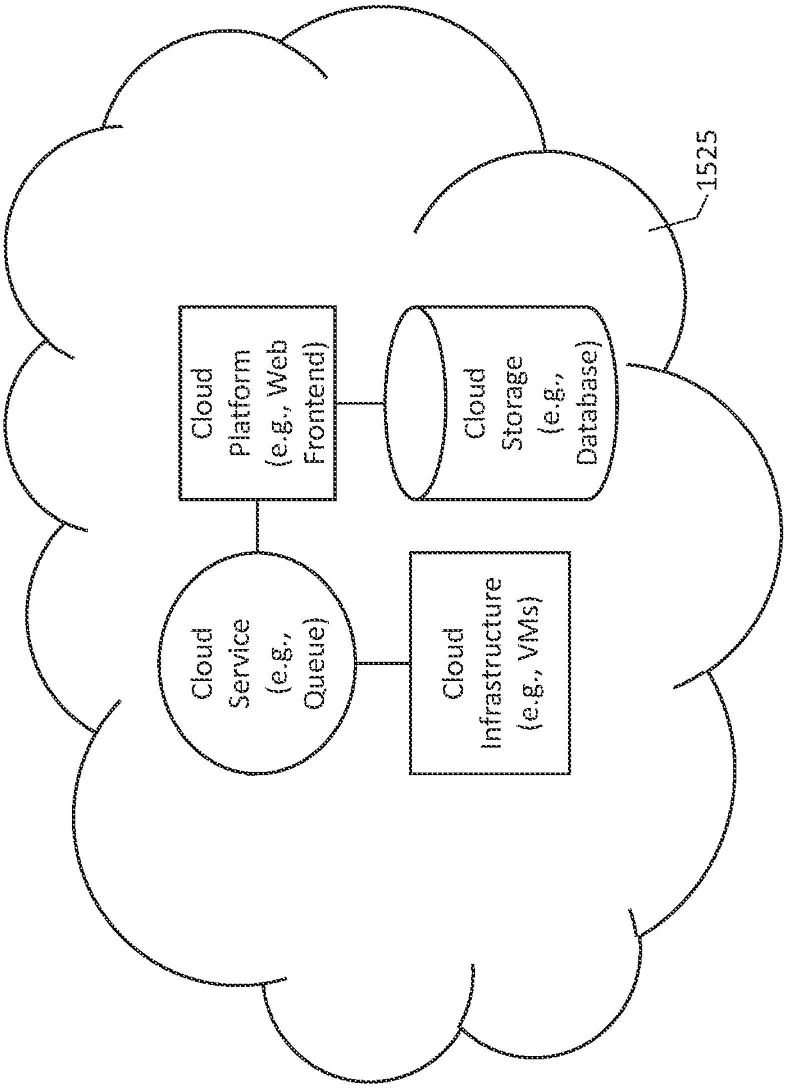
FIG. 16 illustrate schematics of an exemplary implementation of the cloud computing/architecture(s) in which the illustrative computer-based systems or platforms of the present disclosure may be specifically configured to operate.
Figure 17:
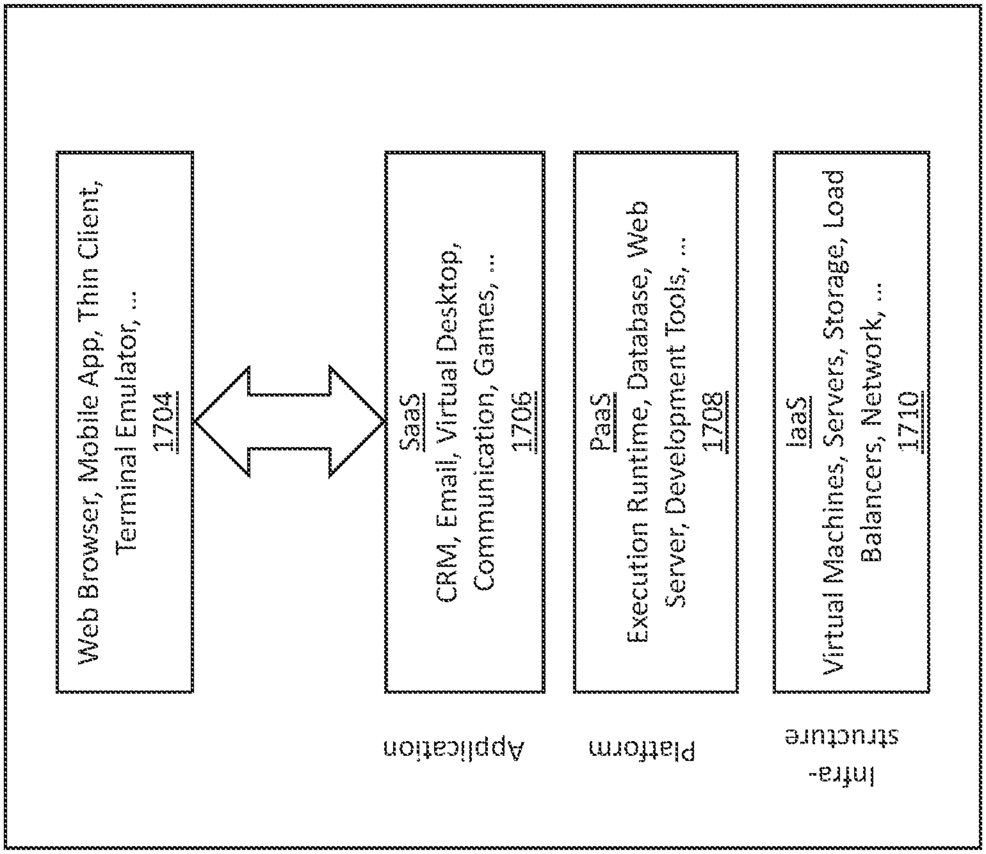
FIG. 17 illustrate schematics of another exemplary implementation of the cloud computing/architecture(s) in which the illustrative computer-based systems or platforms of the present disclosure may be specifically configured to operate.

In some embodiments, the illustrative computer-based systems or platforms of the present disclosure may be specifically configured to operate in a cloud computing/architecture such as, but not limiting to: infrastructure a service (IaaS), platform as a service (PaaS), and/or software as a service (SaaS). FIGS. 16 and 17 illustrate schematics of exemplary implementations of the cloud computing/architecture(s) in which the illustrative computer-based systems or platforms of the present disclosure may be specifically configured to operate.

In some embodiments, exemplary inventive, specially programmed computing systems and platforms with associated devices are configured to operate in the distributed network environment, communicating with one another over one or more suitable data communication networks (e.g., the Internet, satellite, etc.) and utilizing one or more suitable data communication protocols/modes such as, without limitation, IPX/SPX, X.25, AX.25, AppleTalk™, TCP/IP (e.g., HTTP), near-field wireless communication (NFC), RFID, Narrow Band Internet of Things (NBIOT), 3G, 4G, 5G, GSM, GPRS, WiFi, WiMax, CDMA, satellite, ZigBee, and other suitable communication modes. In some embodiments, the NFC can represent a short-range wireless communications technology in which NFC-enabled devices are "swiped," "bumped," "tap" or otherwise moved in close proximity to communicate. In some embodiments, the NFC could include a set of short-range wireless technologies, typically requiring a distance of 10 cm or less.

The material disclosed herein may be implemented in software or firmware or a combination of them or as instructions stored on a machine-readable medium, which may be read and executed by one or more processors. A machine-readable medium may include any medium and/or mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that make the logic or processor. Of note, various embodiments described herein may, of course, be implemented using any appropriate hardware and/or computing software languages (e.g., C++, Objective-C, Swift, Java, JavaScript, Python, Perl, QT, etc.).

In some embodiments, one or more of illustrative computer-based systems or platforms of the present disclosure may include or be incorporated, partially or entirely into at least one personal computer (PC), laptop computer, ultra-laptop computer, tablet, touch pad, portable computer, handheld computer, palmtop computer, personal digital assistant (PDA), cellular telephone, combination cellular telephone/PDA, television, smart device (e.g., smart phone, smart tablet or smart television), mobile internet device (MID), messaging device, data communication device, and so forth.

In some embodiments, illustrative computer-based systems or platforms of the present disclosure may be configured to handle numerous concurrent users that may be, but is not limited to, at least 100 (e.g., but not limited to, 100-999), at least 1,000 (e.g., but not limited to, 1,000-9,999), at least 10,000 (e.g., but not limited to, 10,000-99,999), at least 100,000 (e.g., but not limited to, 100,000-999,999), at least 1,000,000 (e.g., but not limited to, 1,000,000-9,999,999), at least 10,000,000 (e.g., but not limited to, 10,000,000-99,999,999), at least 100,000,000 (e.g., but not limited to, 100,000,000-999,999,999), at least 1,000,000,000 (e.g., but not limited to, 1,000,000,000-999,999,999,999), and so on.

In some embodiments, illustrative computer-based systems or platforms of the present disclosure may be configured to output to distinct, specifically programmed graphical user interface implementations of the present disclosure (e.g., a desktop, a web app., etc.). In various implementations of the present disclosure, a final output may be displayed on a displaying screen which may be, without limitation, a screen of a computer, a screen of a mobile device, or the like. In various implementations, the display may be a holographic display. In various implementations, the display may be a transparent surface that may receive a visual projection. Such projections may convey various forms of information, images, or objects. For example, such projections may be a visual overlay for a mobile augmented reality (MAR) application.

In some embodiments, illustrative computer-based systems or platforms of the present disclosure may be configured to be utilized in various applications which may include, but not limited to, gaming, mobile-device games, video chats, video conferences, live video streaming, video streaming and/or augmented reality applications, mobile-device messenger applications, and others similarly suitable computer-device applications.

In some embodiments, the illustrative computer-based systems or platforms of the present disclosure may be configured to securely store and/or transmit data by utilizing one or more of encryption techniques (e.g., private/public key pair, Triple Data Encryption Standard (3DES), block cipher algorithms (e.g., IDEA, RC2, RCS, CAST and Skipjack), cryptographic hash algorithms (e.g., MD5, RIPEMD-160, RTR0, SHA-1, SHA-2, Tiger (TTH), WHIRLPOOL, RNGs).

The aforementioned examples are, of course, illustrative and not restrictive.

Publications cited throughout this document are hereby incorporated by reference in their entirety. While one or more embodiments of the present disclosure have been described, it is understood that these embodiments are illustrative only, and not restrictive, and that many modifications may become apparent to those of ordinary skill in the art, including that various embodiments of the inventive methodologies, the illustrative systems and platforms, and the illustrative devices described herein can be utilized in any combination with each other. Further still, the various steps may be carried out in any desired order (and any desired steps may be added and/or any desired steps may be eliminated).

The invention claimed is:

1. A method comprising:

receiving, by at least one processor, at least one data stream comprising wearable sensor data associated with a user;

wherein the at least one data stream comprises biomarker data parameters indicative of cardiac activity;

utilizing, by the at least one processor, seizure forecasting machine learning model to predict a pre-ictal period probability associated with a forecasted time segment based at least in part on values of the at least one data stream, the seizure forecasting machine learning model comprising at least one neural network having parameters trained on seizure training data;

determining, by the at least one processor, a segment for an integration window of a history of pre-ictal period probabilities for the forecasted time segment and at least one previously forecasted time segment;

determining, by the at least one processor, a pre-ictal period based at least in part on the segment exceeding a pre-ictal probability threshold;

determining, by the at least one processor, a pre-ictal risk indication including a seizure treatment administration responsive to the pre-ictal risk indication; and causing to produce, by the at least one processor, the pre-ictal risk indication at a computing device associated with the user to alert the user of a predicted risk of a seizure.

2. The method as recited in claim 1, further comprising communicating, by the at least one processor, with a wearable device to receive the at least one data stream in real-time.

3. The method as recited in claim 2, wherein the wearable device includes a biomarker sensor worn by the user.

4. The method as recited in claim 1, wherein the at least one data stream comprises:

i) electrodermal activity,
ii) heart rate,
iii) blood volume pulse,
iv) temperature,
v) accelerometer-based movement data
vi) electroencephalogram measurements,
vii) time,
viii) date,
ix) global positioning system data,
x) medication,
xi) self-reported seizures,
xii) clinical patient data, or
xiii) combinations thereof.

5. The method as recited in claim 1, wherein the time segment used to calculate forecasts comprises thirty seconds.

6. The method as recited in claim 1, wherein the integration window comprises a rolling three hundred second period of the history of pre-ictal period probabilities.

7. The method as recited in claim 1, further comprising determining, by the at least one processor, an inter-ictal period upon the pre-ictal period probability falling below the pre-ictal probability threshold.

8. The method as recited in claim 1, further comprising modifying, by the at least one processor, a time-span of the integration window, a time span of the forecasted time segment, the pre-ictal probability threshold, seizure occurrence period, or combinations thereof, based on an accuracy of the pre-ictal risk alert for the user.

9. A system comprising:

at least one sensor; and at least one processor in communication with the at least one sensor and configured to perform steps of instructions stored in a non-transitory memory, the steps comprising:

receive from the at least one sensor at least one data stream associated with a user indicative of cardiac activity;

wherein the at least one data stream comprises biomarker data parameters;

utilize seizure forecasting machine learning model to predict a pre-ictal period probability associated with a forecasted time segment based at least in part on values of the at least one data stream, the seizure forecasting machine learning model comprising at least one neural network having parameters trained on seizure training data;

determine a segment value for an integration window of a history pre-ictal period probabilities for the forecasted time segment and at least one previously forecasted time segment;

determine a pre-ictal period based at least in part on the segment value exceeding a pre-ictal probability threshold;

determine a pre-ictal risk indication including a seizure treatment administration responsive to the pre-ictal risk indication; and cause to produce a pre-ictal risk indication at a computing device associated with the user to indicate a predicted risk of a seizure.

10. The system as recited in claim 9, wherein the at least one processor is further configured to generate a pre-ictal risk alert to alert the user of the predicted seizure.

11. The system as recited in claim 9, wherein the at least one processor is further configured to generate a risk profile based on a history of pre-ictal risk indicators associated with the user.

12. The system as recited in claim 11, wherein the at least one processor is further configured to generate treatment plan optimizations for mitigating seizures.

13. The system as recited in claim 9, wherein the at least one processor is further configured to generate a seizure mitigation suggestion based on the pre-ictal risk indicator and the at least one data stream.

14. The system as recited in claim 13, wherein the seizure mitigation suggest comprises one or more of:

i) a medication administration,
ii) a release of stimulation, or
iii) a combination thereof.

15. The system as recited in claim 9, wherein the at least one processor is further configured to communicate with a wearable device to receive the at least one data stream in real-time.

16. The system as recited in claim 15, wherein the wearable device includes a wrist worn sensor.

17. The system as recited in claim 9, wherein the at least one data stream comprises:

i) electrodermal activity,
ii) heart rate,
iii) blood volume pulse,
iv) temperature,
v) accelerometer-based movement data, or
vi) electroencephalogram measurements,
vii) time,
viii) date,
ix) global positioning system data,
x) medication,
xi) self-reported seizures,
xii) clinical patient data, or
xii) combinations thereof.

18. The system as recited in claim 9, wherein the at least one processor is further configured to determine an interictal period upon the pre-ictal period probability falling below the pre-ictal probability threshold.

* * * * *